(12) United States Patent
Masoud

(10) Patent No.: US 9,808,326 B2
(45) Date of Patent: Nov. 7, 2017

(54) 3D DENTOFACIAL SYSTEM AND METHOD

(71) Applicants: PRESIDENT AND FELLOWS OF HARVARD COLLEGE, Cambridge, MA (US); TRUSTEES OF BOSTON UNIVERSITY, Boston, MA (US)

(72) Inventor: Mohamed I. Masoud, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/661,820

(22) Filed: Mar. 18, 2015

(65) Prior Publication Data

US 2015/0265374 A1    Sep. 24, 2015

Related U.S. Application Data

(60) Provisional application No. 61/954,835, filed on Mar. 18, 2014.

(51) Int. Cl.
*G06K 9/00* (2006.01)
*A61C 7/00* (2006.01)
(Continued)

(52) U.S. Cl.
CPC ............ *A61C 7/002* (2013.01); *A61B 5/0088* (2013.01); *A61B 34/10* (2016.02);
(Continued)

(58) Field of Classification Search
None
See application file for complete search history.

(56) References Cited

U.S. PATENT DOCUMENTS 7,699,607 B2 * 4/2010 Margossian ......... A61C 19/045
                                                      33/511
7,717,708 B2    5/2010 Sachdeva et al.
(Continued)

OTHER PUBLICATIONS

Alqattan et al., "Comparison between landmark and surface-based three-dimensional analyses of facial asymmetry in adults", European Journal of Orthodontics, published Oct. 23, 2013.*
(Continued)

*Primary Examiner* — Soo Park
(74) *Attorney, Agent, or Firm* — Nixon Peabody LLP; David S. Resnick; David F. Crosby

(57) ABSTRACT

A reference standard or reference system for dental feature location and orientation can include evaluating the facial appearance of one or more subjects based on aesthetic criteria and selecting a subset of subjects. The reference standard further includes constructing 3D representations, (e.g., a 3D virtual model), of the facial and dental features of the subset of subjects, from photographs of the face and mouth of each subject and determining the location and/or orientation of one or more dental features for each subject. The location and/or orientation values for each subject can be used to produce an average value and a standard deviation that forms the basis for a reference standard as part of reference system for evaluating patients. The method and system further includes constructing 3D representations (e.g., a 3D virtual model) of the facial and dental features of a patient from photographs of the face and mouth of the patient and determining the location and/or orientation of one or more dental features of the patient in order to compare them to the reference standard and develop a treatment plan for the subject based on differences between the patient's measurements and reference standard. The reference standard can use the pupils (e.g., in the natural head position orientation) as a landmark for registration and scaling of the reference standard to the patient under evaluation.

15 Claims, 16 Drawing Sheets
(16 of 16 Drawing Sheet(s) Filed in Color)

(51) Int. Cl.
     A61B 5/00        (2006.01)
     A61B 34/10       (2016.01)
(52) U.S. Cl.
     CPC ..... *G06K 9/00208* (2013.01); *G06K 9/00281* (2013.01); *A61B 2034/105* (2016.02); *A61B 2576/02* (2013.01); *A61C 2007/004* (2013.01); *G06K 2209/055* (2013.01)

(56) References Cited

U.S. PATENT DOCUMENTS

| | | | | |
|---|---|---|---|---|
| 7,833,013 | B2* | 11/2010 | Diers | A61B 5/1072 351/204 |
| 8,021,147 | B2* | 9/2011 | Sporbert | A61C 7/00 433/24 |
| 8,496,474 | B2 | 7/2013 | Chishti et al. | |
| 2012/0010533 | A1* | 1/2012 | Arnett | A61B 5/0064 600/590 |
| 2014/0329194 | A1* | 11/2014 | Sachdeva | A61C 7/002 433/24 |
| 2014/0348405 | A1* | 11/2014 | Chen | G06T 7/0046 382/131 |

OTHER PUBLICATIONS

Unknown author, "What's new in Dolphin Imaging 11.7", available online at http://www.dolphinimaging.info/download/2013-11.5-Slicks/What'sNewVersion11.7.pdf, dated Feb. 24, 2014.*

Sforza et al., "Three-dimensional facial asymmetry in attractive and normal people from childhood to young adulthood", Symmetry 2010, 2, 1925-1944.*

Swennen et al., "Three-dimensional treatment planning of orthognathic surgery in the era of virtual imaging", 2009 American Association of Oral and Maxillofacial Surgeons.*

Toma et al., "The assessment of facial variation in 4747 British school children", European Journal of Orthodontics, published Sep. 20, 2011.*

3M ESPE Lava Chairside Oral Scanner User Guide Version 2.0 (2009).

Adams et al., "Geometric morphometrics: Ten years of progress following the revolution", Ital. J. Zool, 71:5-16 (2004).

Albarakati et al., "The Reliability and Reproducibility of cephalometric measurements: a comparison of conventional and digital methods", Dentomaxillofac Radiol, 41(1):11-17 (2012).

Arnett et al., "Soft tissue cephalometric analysis: diagnosis and treatment planning of dentofacial deformity", Am J Orthod Dentofacial Orthop,116(3):239-53 (1999).

Azar, Thesis: "The Consistency of Orthodontic Diagnosis and Treatment Planning", Saint Louis University, (2012). 82pp.

Baccetti et al., "The Cervical Vertebral Maturation (CVM) Method for the Assessment of Optimal Treatment Timing in Dentofacial Orthopedics" Seminars in Orthodontics, 11:119-29 (2005).

Botticelli et al., "Two versus three-dimensional imaging in subjects with unerupted maxillary canines", Eur J Orthod, 33:344-9 (2011).

Broadbent, "A new X-ray technique and its application to orthodontia: the introduction of cephalometric radiography" The Angle Orthodontist, 1(2):45-66 (1931).

Cunningham et al., "Their ideas of beauty are, on the whole, the same as ours": Consistency and variability in the cross-cultural perception of female physical attractiveness, Journal of Personality and Social Psychology, 68(2):261-279 (1995).

Durao et al., "Validity of 2D lateral cephalometry in orthodontics: a systematic review", Prog Orthod, 14:31 (2013).

European Commission 1997 Council Directive 97/43/Euratom on health protection of individuals against the dangers of ionizing radiation in relation to medical exposure. Official Journal of the European Communities, No. L180/22-27.9.07. European Commission, Luxembourg, pp. 22-27.

European Commission. Radiation Protection 136. European guidelines on radiation protection in dental radiology. Luxembourg: Office for Official Publications of the European Communities; 2004 available at: https://ec.europa.eu/energy/sites/ener/files/documents/136.pdf.

Fleming et al., "Orthodontic measurements on digital study models compared with plaster models: a systematic review", Orthod Craniofac Res.14:1-16 (2011).

Gangestad et al., "Pathogen prevalence and human mate preferences", Ethol Sociobiol, 14:89-96 (1993).

Haghi, Thesis: "The Validation of a Non-Radiation Technique for Orthodontic Diagnosis That Involves Three Dimensional Dentofacial Images" Boston University Goldman School of Dental Medicine (2014). 106pp.

Hajeer et al., "Current Products and Practices Applications of 3D imaging in orthodontics: Part II" Journal of Orthodontics, 31:154-162 (2004).

Hartmann, "Considerations in the Choice of Interobserver Reliability Estimates" Journal of Applied Behavior Analysis, 10:103-116 (1977).

Huanca Ghislanzoni et al., "Evaluation of tip and torque on virtual study models: a validation study" Prog Orthod, 14(1):19 (2013).

Hujoel et al., "Head-and-neck organ doses from an episode of orthodontic care", Am J Orthod Dentofacial Orthop, 133:210-7 (2008).

Hume et al., "Facial attractiveness signals different aspects of quality in women and men", Evol Hum Behav, 22(2):93-112 (2001).

Ishaq et al., "Insulin-like growth factor I: abiological maturation indicator", Am J Orthod Dentofacial Orthop, 142(5):654-61 (2012).

Keim et al., "2002 JCO study of orthodontic diagnosis and treatment procedures. Part 1. Results and trends", Journal of Clinical Orthodontics,36:553-568 (2002).

Larson, "Cone-beam computed tomography is the imaging technique of choice for comprehensive orthodontic assessment", Am J Orthod Dentofacial Orthop, 141(4):402, 404, 406 (2012).

Leung et al., "Accuracy and reliability of cone-beam computed tomography for measuring alveolar bone height and detecting bony dehiscences and fenestrations", Am J Orthod Dentofacial Orthop, 137(4 Suppl):S109-19 (2010).

Lie et al., "Genetic diversity revealed in human faces", Evolution, 62(10):2473-86 (2008).

Ludlow et al., "Phantom dosimetry and image quality of i-CAT FLX cone-beam computed tomography", Am J Orthod Dentofacial Orthop, 144(6):802-17 (2013).

Lundstrom et al., "A proportional analysis of the soft tissue facial profile in young adults with normal occlusion", Angle Orthod, 62(2):127-33 (1992).

Masoud et al., "Assessing skeletal maturity by using blood-spot insulin-like growth factor I (IGF-I) testing", Am J Orthod Dentofacial Orthop, 134(2):209-16 (2008).

Moore et al., "A critique of orthodontic dogma", Angle Orthod, 39(2):69-82 (1969).

Nijkamp et al., "The influence of cephalometrics on orthodontic treatment planning", Eur J Orthod, 30(6):630-5 (2008).

Ongkosuwito et al., "The reproducibility of cephalometric measurements: a comparison of analogue and digital methods", Eur J Orthod, 24:655-665 (2002).

Pauwels et al., "The Sedentexct Project Consortium. Effective dose range for dental cone beam computed tomography scanners" Eur J Radiol, 81:267-71 (2012).

Peck et al., "A Concept of Facial Esthetics", The Angle Orthodontist, 40(4):284-317 (1970).

Perinetti et al., "Gingival crevicular fluid alkaline phosphatase activity as a non-invasive biomarker of skeletal maturation", Orthod Craniofac Res, 14(1):44-50 (2011).

Petersson, "What you can and cannot see in TMJ imaging—an overview related to the RDC/TMD diagnostic system", J Oral Rehabil, 37:771-8 (2010).

Pittayapat et al., "Three-dimensional cephalometric analysis in orthodontics: a systematic review", Orthod Craniofac Res, 17(2):69-91 (2014).

(56) References Cited

OTHER PUBLICATIONS

Plooij et al., "Evaluation of reproducibility and reliability of 3D soft tissue analysis using 3D stereophotogrammetry" Int J Oral Maxillofac Surg, 38(3):267-73 (2009).

Proffit et al., "Changes in the pattern of patients receiving surgical-orthodontic treatment", Am J Orthod Dentofacial Orthop, 143(6):793-8 (2013).

Rhodes et al., "Are average facial configurations attractive only because of their symmetry?", Psychol Sci, 10(1):52-8 (1999).

Rhodes et al., "Attractiveness of facial averageness and symmetry in non-western cultures: in search of biologically based standards of beauty", Perception, 30(5):611-25 (2001).

Rischen et al., "Records needed for orthodontic diagnosis and treatment planning: a systematic review", PLoS One, 8(11):e74186 (2013).

Smith et al., "An evaluation of cone-beam computed tomography use in postgraduate orthodontic programs in the United States and Canada" J Dent Educ, 75:98-106 (2011).

Stemler, "A comparison of consensus, consistency, and measurement approaches to estimating interrater reliability", Practical Assessment, Research & Evaluation, 9(4) (2004).

Timock et al., "Accuracy and reliability of buccal bone height and thickness measurements from cone-beam computed tomography imaging", Am J Orthod Dentofacial Orthop, 140:734-44 (2011).

Turpin, "British Orthodontic Society revises guidelines for clinical radiography", Am J Orthod Dentofacial Orthop, 134(5):597-8 (2008).

Van Vlijmen et al., "Evidence supporting the use of cone-beam computed tomography in orthodontics", J Am Dent Assoc,143(3):241-52 (2012).

Wall et al., "What are the risks from medical X-rays and other low dose radiation?", Br J Radiol, 79(940):285-94 (2006).

Whetten et al., "Variations in orthodontic treatment planning decisions of class II patients between virtual 3-dimensional models and traditional plaster study models", Am J Orthod Dentofacial Orthop, 130:485-491 (2006).

White, "Assessment of radiation risk from dental radiography", Dentomaxillofac Radiol, 21:118-26 (1992).

Dolphin Imagining & Management Solutions, "Ceph Tracing", Dolphin Imaging 11.7 Beta (2013). Web. (www.dolphinimaging.com).

Sforza et al., "Soft-Tissue Facial Characteristics of Attractive Italian Women as Compared to Normal Women", The Angle Orthodontist, 79(1):17-23 (2009).

Adamson et al., "Changing perceptions of beauty: a surgeon's perspective", Facial Plast Surg, 22(3):188-93 (2006).

Atchinson et al., "An algorithm for ordering pretreatment orthodontic radiographs", Am J Orthod Dentofacial Orthop, 102:29-44 (1992).

Bozic et al., "Novel method of 3-dimensional soft-tissue analysis for Class III patients" Am J Orthod Dentofacial Orthop. 138(6):758-69 (2010).

Bruks et al., "Radiographic examinations as an aid to orthodontic diagnosis and treatment planning", Swed Dent J, 23(2-3):77-85 (1999).

Buss "The Evolution of Desire (Second ed.)" New York: Basic Books. pp. 54, 55 (2003)[1994].

Carlsson et al., "Crown-root angles of upper central incisors", Am J Orthod, 64(2):147-54 (1973).

Cellerino, "Psychobiology of facial attractiveness", J Endocrinol Invest, 26(3 Suppl):45-8 (2003).

Cunningham, "Measuring the Physical in Physical Attractiveness: Quasi-Experiments on the Sociobiology of Female Facial Beauty", Journal of Personality and Social Psychology, 50(5):925-935 (1986).

Dijkstal et al., "Normal exophthalmometry measurements in a United States pediatric population", Ophthal Plast Reconstr Surg, 28(1):54-6 (2012).

English et al., "Individuality of human palatal rugae", J Forensic Sci, 33:718-26 (1988).

Farkas et al., "Geography of the nose: a morphometric study" Aesthetic Plast Surg, 10(4):191-223 (1986).

Gower, "Generalized procrustes analysis", Psychometrika, 40:31-33 (1975).

Halazonetis, "Cone-beam computed tomography is not the imaging technique of choice for comprehensive orthodontic assessment", Am J Orthod Dentofacial Orthop, 141(4):403, 405, 407 (2012).

Hellman, "The face and occlusion of the teeth in man", International Journal of Orthodontia, Oral Surgery and Radiography, 13(11):921-45 (1927).

Hintze et al., "Diagnostic value of clinical examination for the identification of children in need of orthodontic treatment compared with clinical examination and screening pantomography", Eur J Orthod, 12(4):385-8 (1990).

Iliffe, "A study of prefences in feminine beauty", Brit J pshycol, 51:267 (1960).

Jacobson, "The "Wits" appraisal of jaw disharmony", Am J Orthod, 67(2):125-38 (1975).

Kochel et al., "3D soft tissue analysis—part 1:sagittal parameters", J Orofac Orthop. 71(1):40-52 (2010).

Kochel et al., "3D soft tissue analysis—part 2: vertical parameters", J Orofac Orthop. 71(3):207-20 (2010).

Kohl "The mind's eyes: Human pheromones, neuroscience, and male sexual preferences" Journal of Psychology & Human Sexuality, 18(4):313-369 (2007).

Lagravere et al., "Intraexaminer and interexaminer reliabilities of landmark identification on digitized lateral cephalograms and formatted 3-dimensional cone-beam computerized tomography images", Am J Orthod Dentofacial Orthop, 137(5):598-604 (2010).

Langlois et al., "Attractive Faces Are Only Average", Psychol Sci, 1(2):115-21 (1990).

Lee et al., "Consistency of orthodontic treatment planning decisions", Clin Orthod Res, 2(2):79-84 (1999).

Lewis, "Why are mixed-race people perceived as more attractive?", Perception, 39(1):136-8 (2010).

Lundstrom et al., "Natural head position and natural head orientation: basic considerations in cephalometric analysis and research", Eur J Orthod, 17(2):111-20 (1995).

Maclachlan et al., "Normal values and standard deviations for pupil diameter and interpupillary distance in subjectsaged 1 month to 19 years", Ophthalmic Physiol Opt, 22(3):175-82 (2002).

Martin, Racial ethnocentrism and judgment of beauty, J Soc Psychol, 63:59-63 (1964).

Masoud et al., "Prospective longitudinal evaluation of the relationship between changes in mandibular length and blood-spot IGF-1 measurements", Am J Orthod Dentofacial Orthop, 141(6):694-704 (2012).

Masoud et al., "Relationship between blood-spot insulin-like growth factor 1 levels and hand-wrist assessment of skeletal maturity", Am J Orthod Dentofacial Orthop, 136(1):59-64 (2009).

Moorrees et al., "New norms for the mesh diagram analysis", Am J Orthod, 69(1):57-71 (1976).

Remedios et al., "Making the best use of clinical radiology services: a new approach to referral guidelines", Clinical Radiology, 62:919-20 (2007).

Rhodes et al., "Attractiveness of own-race, other-race, and mixed-race faces", Perception, 34(3):319-40 (2005).

Rhodes et al., "Averageness, Exaggeration, and Facial Attractiveness", Psychol Sci, 7(2):105-10 (1996).

Rhodes, "The evolutionary psychology of facial beauty", Annu Rev Psychol, 57:199-226 (2006).

Riedel, "An analysis of dentofacial relationships" Amer. J. Orthodont, 43:103-119 (1957).

Ruf, "TMD and the daily orthodontic practice." World J Orthod 6.Suppl:210 (2005).

Sandler, "Reproducibility of cephalometric measurements", Br J Orthod, 15(2):105-10 (1988).

Srinivasan et al., "Relationship between crown-root angulation (collum angle) of maxillary central incisors in Class II, division 2 malocclusion and lower lip line", Orthodontics (Chic.), 14(1):e66-74 (2013).

Steiner, "Cephalometrics for you and me", American Journal of Orthodontics, 39(10):729-55 (1953).

(56) References Cited

OTHER PUBLICATIONS

Taylor, "Variation in form of human teeth: I. An anthropologic and forensic study of maxillary incisors", J Dent Res, 48(1):5-16 (1969).
Thornhill et al., "Human facial beauty : Averageness, symmetry, and parasite resistance", Hum Nat, 4(3):237-69 (1993).
Udry, "Structural correlates feminie beauty preferences in britain and the united states: a comparision", Socio and Social Res, 49:330 (1965).
Vincent et al., "Cephalometric landmark identification error", Aust Orthod J, 10(2):98-104 (1987).

* cited by examiner

3D DENTOFACIAL SYSTEM AND METHOD

CROSS-REFERENCE TO RELATED APPLICATIONS

This application claims benefit under 35 U.S.C. §119(e) of the U.S. Provisional Application No. 61/954,835, filed on Mar. 18, 2014, the contents of which are incorporated herein by reference in their entirety.

STATEMENT REGARDING FEDERALLY SPONSORED RESEARCH

Not Applicable

REFERENCE TO MICROFICHE APPENDIX

Not Applicable

BACKGROUND

Technical Field of the Invention

The present invention is directed to methods and systems for evaluating the facial and dental features of a patient for orthodontic diagnosis and treatment. The present invention is directed to methods and systems for establishing a standard for alignment of dental features of a patient and to methods and systems for comparing the facial and dental features of a patient to the standard to assist in developing a treatment plan and evaluating progress during treatment.

Description of the Prior Art

Before Broadbent [1] Introduced cephalometric radiography in 1931, Orthodontic diagnosis depended on the orthodontist's clinical judgment of the patient's face and the malocclusion of the teeth. Milo Helman [2] did extensive work on photographic norms and advocated systematically measuring and analyzing the face. However, the introduction of radiographic cephalometrics overwhelmed those efforts.

Broadbent concluded that the Sella and Nasion (cephalometric landmarks) were the most stable parts of the area he exposed and suggested their use as stable reference points for diagnosing discrepancies and monitoring growth and treatment changes.

In 1953 Steiner [3] wrote, "It has been claimed by many that it is a tool of the research laboratory and that the difficulties and expense of its use in clinical practice are not justified. Many have argued that the information gained from cephalometric films, when used with present methods of assessment, do not contribute sufficient information to change, or influence, their plans of treatment."

Since then, the cephalometric radiograph has been the subject of most of our diagnostic attention with analysis after analysis focusing on the cranial base as the reference for measuring deviations from what is referred to as the "Norm."

Studies [4][5][6] have demonstrated individual variations in the orientation of the jaws and/or cranial base that make many of the classical measurements irrelevant. Sella and Nasion both show great individual variation in their position and Nasion continues to grow into a patient's teens. A low sella can result in a normally positioned maxilla having hypoplastic readings and a short cranial base can result in a class I skeletal relationship having class II measurements.

Others have suggested going back to traditional anthropological reference planes like Frankfort's Horizontal which was considered to best compromise for the orientation of crania of nonliving subjects. Moorrees [5] demonstrated that although Frankfort was relatively reproducible, it could vary up to 10 degrees from a living persons natural Orientation. Since we work with living individuals, he introduced orthodontists to the concept of Natural Head Position, which is determined by having a subject look at a distant object (e.g., the horizon) or his or her own eyes in a mirror. [6] This was shown to be reproducible to within 1-2 degrees and is considered the most accurate physiological reference line. True Horizontal as determined by Natural head positions was the bases for Moorrees's Mesh analyses which involved a scaled template of an ideal face that would be overlaid on the patient's face superimposing on Nasion and oriented according to Natural head position to visually determine the amount and location of dental and skeletal discrepancies. The distance between Sell and Nasion was used for scaling but the analysis did not really measure discrepancies relative to the position of landmarks inside the cranial base. The Concepts and ideas involved in this method provided orthodontists the tools to reduce their dependence on cephalometric radiography but still involved scaling to cranial base measurements and superimposing on Nasion which require radiographic exposure of the upper third of the face. Implant studies have also shown that Nasion experiences significant sutural growth in teenagers rendering the measurement of growth or treatment relative to it inaccurate.

Despite the progress Moorrees made in changing the paradigm, the profession reverted to its plaster models, its 2d photos and comparing radiographic measurements to reference values that do not necessarily represent what our patient populations seeks.

These so called "Norms" did not actually represent the average of the population and were almost all selected based on the author of a particular analysis's judgment of the occlusion and/or the face. Orthodontists may be the best candidates for judging the occlusion but their perception of facial esthetics can be influenced by their training and may not represent what the public finds attractive. This was demonstrated by Peck and Peck [7] in 1970 when they demonstrated that cephalometric measurements of people the public considered attractive at that time were generally "fuller and more protrusive" than the reference values of the commonly used cephalometric analyses.

Neotenized (childish) faces were found to be consistently more attractive regardless of the subject's actual age [8][9][10][11], and research has showed large agreement on characteristics of attractive faces across different racial and ethnic backgrounds. [12] Computer generated images with more average features were considered more attractive. [13] A composite formed by blending faces and averaging the features produced a face that was considered more attractive than most of the faces used to create it. However, in females enhancing certain female specific and species specific traits (e.g., smaller than average noses and chins, and higher than average foreheads) made the resulting face more attractive to males than the composite. Female preference for male faces was more variable and even varied with hormonal status, changes in the menstrual cycle, and contraceptive hormonal treatment. [14] Facial averageness and Symmetry were found to be attractive in Western and non-western cultures. Faces that were made more symmetric and closer to an average composite were considered more attractive and vise a versa. There was also no preference for own race composites over other races or mixed race composites. [15]

Several studies [7][6][17] have described soft tissue analyses. Most used two-dimensional images and several recent articles have used 3-dimensional images. The measurements performed generally resembled cephalometric measurements, and consistent statistically significant correlations were found between the cephalometric and soft tissue measurement. [18][19] Plooij [20] studied the reproducibility of 49 landmarks on 3D facial images and found that the intraobserver differences of 45 landmarks were less than 0.5 mm. The interobserver differences for 39 landmarks were less than 0.5 mm In 2010, Božič [21] presented a method of 3D soft tissue analysis that involved comparing patients to a 3D soft tissue template that was developed by averaging faces with class I occlusal relationships. Color-coding was used to mark parts of the face that deviated from the template used as the standard. The method described was a significant departure from the traditional diagnostic methods. However, like previous soft tissue analyses, the dentition was not evaluated within the context of the soft tissue making these methods adjuncts to cephalometrics and not potential replacements.

3D dental imaging has been available for over a decade and has been validated and widely accepted as an alternative to traditional casts for orthodontic diagnosis. [22][23]

Technology has evolved but orthodontists are essentially doing exactly what they did 80 years ago using computers to measure what they used to measure manually. Cephalometric radiographs continue to be the cornerstone of orthodontic diagnosis despite the fact that research has shown that cephalometric radiographs have no impact on treatment planning decisions regardless of the orthodontist's experience. [24]. An AJODO editorial reviewing recent radiation exposure guidelines for orthodontists mentions that there is no safe level of radiation exposure and that the benefits of diagnostic radiology usually outweigh the risks involved. [25] It concludes that there should not be a set of routine radiographs for all orthodontic patients, and that the risk involved is only justified when there is a health benefit to the patient from a minimum dose. It is unnecessary to take radiographs for routine investigation of TMD, for post treatment or prospective radiographs for medico-legal reasons, or for professional examinations. [25][26][27][28][29]

Despite these guidelines some orthodontists [30][31][32] are advocating routinely exposing patients to many times the radiographic exposure of a cephalometric radiograph through cone beam imaging (68-368 μSv vs 30 μSv for a panoramic and cephalometric radiograph together). If every patient starting orthodontic treatment in the United States each year had one cone beam image instead of a cephalometric and panoramic radiograph, there would statistically be 10-80 additional cancer patients per year. [33][34][35] Most people advocating the use of cone beam radiographs end up converting them into 2-dimensional images and perform traditional cephalometric measurements so it is unclear why that would be expected to provide any more information than traditional cephalometric radiograph? Typical resolution is 0.3 to 0.4 voxels which results in lower resolution than traditional radiographs, greater error in identifying landmarks, underestimation of alveolar bone height, and overestimation fenestration and dehiscence. [36][37] They have limited usefulness even in patients with tempormandibular joint disorders since most of these are soft tissue in origin with radiographic changes usually appearing after the acute phase has passed. There is also no evidence to support that they aid in providing better treatment of these conditions. [38][39]

Two independent systematic reviews conducted in 2012 and 2013 [40][41] concluded that there is no high quality evidence to support the usefulness of cone beam imaging in orthodontics. In certain situation they can aid in the diagnosis and treatment of impacted teeth but even that could be done by only exposing the area of interest. [42]

Orthodontists are facing the same questions Cecile Steiner had to answer over 50 years ago. In a paper [43] that studied Head and neck organ radiographic doses, Hujoel et al. wrote: "Today, just like orthodontic radiography in the early 1900s, CBCT for orthodontic therapy is advocated by experts, without reliable evidence that the diagnostic technology is associated with improved patient outcomes."

The area orthodontic treatment can influence is generally limited to the lower third of the face and if orthodontists are radiographically exposing the rest of the cranium to simply use it as a reference they need to stop and ask themselves if there is a deferent part of the face that can serve that purpose without the radiation involved in viewing the cranial base.

In late 2013 a systematic review[44] evaluating orthodontic records concluded: "Cephalograms are not routinely needed for orthodontic treatment planning in Class II malocclusions, digital models can be used to replace plaster casts, and cone-beam computed tomography radiographs can be indicated for impacted canines. Based on the findings of this review, the minimum record set required for orthodontic diagnosis and treatment planning could not be defined." They also mentioned that the influence of 3D facial imaging on diagnosis, treatment planning, and outcome assessment has not yet been evaluated. [44]

SUMMARY

Although some investigators 18, 19, 21 have studied the accuracy of 3D facial imaging as well as 3D facial standards, no study to date has combined the 3D facial images together with 3D dental images and established standards for their use to diagnose dentofacial discrepancies and measure growth and treatment changes. The absence of the teeth within the context of the face is probably the main factor that has hindered the routine use of this technology since orthodontists still have to rely on cephalometric norms to determine the position of the and inclination of the teeth.

One object of the invention is to provide a non-radiographic technique to diagnose orthodontic and dentofacial problems and evaluate progress and outcomes. Other objects of the invention can include: A) to use the eyes as stable part of the face that is visible to the naked eye as a reference, B) to accurately record the dentofacial structures in their natural and reproducible orientation that best represents the actual patient, C) to establish a method and system to determine the location and orientation of the teeth and facial structures, D) to establish a method and system to compare the location of the dentofacial structures of a patient to a comparable standard that represents the esthetic ideal that the public consider attractive as well as the functional occlusal relationships that are valued by the orthodontic profession.

These and other capabilities of the invention, along with the invention itself, will be more fully understood after a review of the following figures, detailed description, and claims.

BRIEF DESCRIPTION OF THE FIGURES

This patent or application file contains at least one drawing executed in color. Copies of this patent or patent application publication with color drawing(s) will be provided by the Office upon request and payment of the necessary fee.

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

DETAILED DESCRIPTION OF PREFERRED EMBODIMENTS

Figure 1:
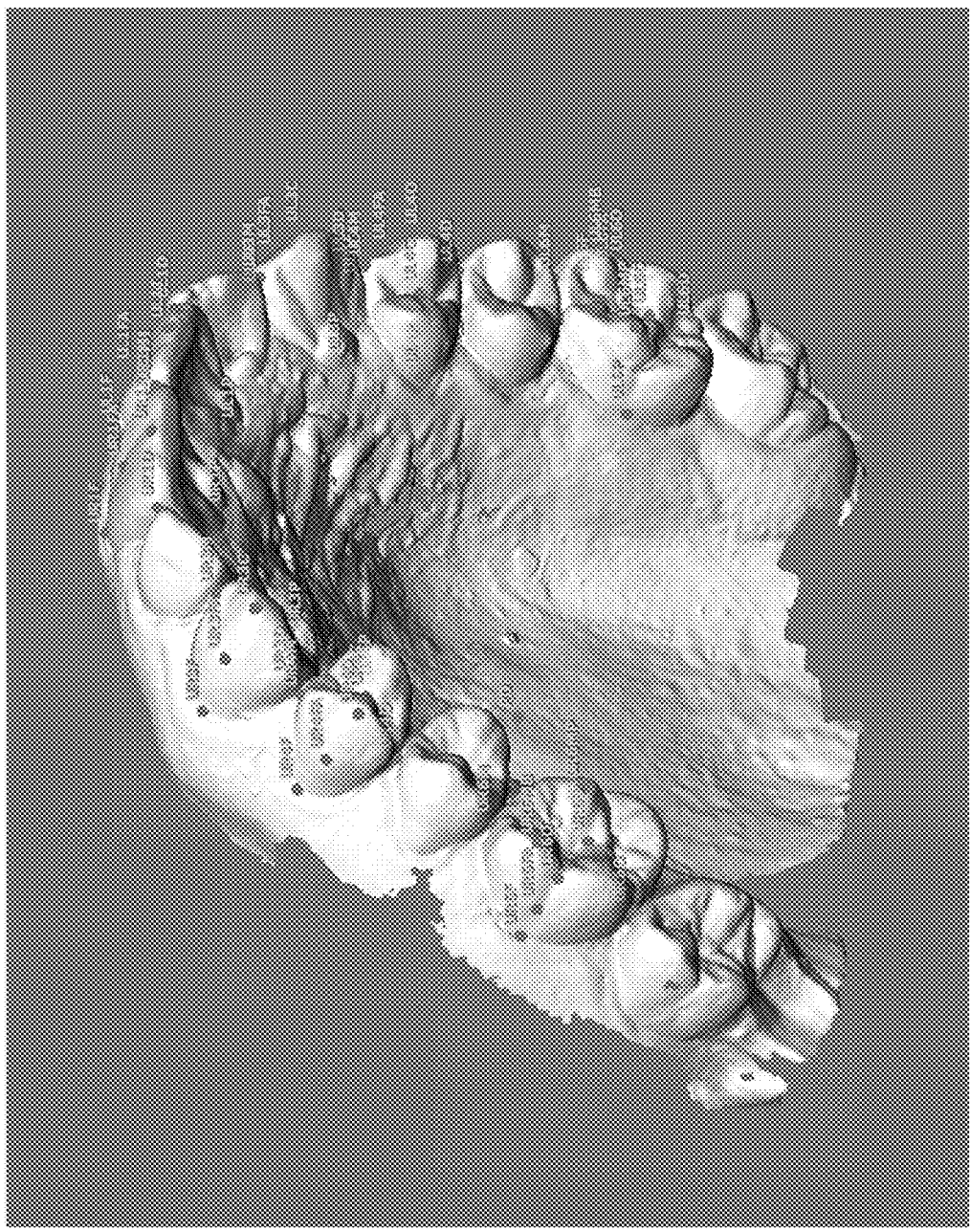
FIG. 1 is a diagram of an upper jaw marked with dental landmarks according to some embodiments of the invention.

The present invention is directed to methods and systems for establishing a standard or reference system for facial and dental feature location and orientation and to methods and systems for determining the location and orientation of facial and dental features of a subject by comparing them to a standard, and developing a treatment plan for the subject. The present invention also includes methods and systems for determining the effectiveness of treatment and for modifying the treatment. The present invention also includes methods and systems for evaluating outcomes and for determining whether additional treatment can or should be provided.

In accordance with embodiments of the invention, the standard or reference system can include a reference framework that forms the basis for positioning (e.g., the measurement of position and orientation) of facial and dental features. Thus, for example, the standard can define a position and orientation in 3 dimensional (3D) space of a dental feature (e.g., a tooth, such an upper right canine) with respect to one or more planes that make up the reference framework of the reference system. The reference system can include one or more sets of tables that define the reference planes and the distance between a landmark on a facial feature (e.g., center of the pupils or bridge of the nose) or dental feature (e.g., a point on a tooth) and one or more reference planes. The reference system can also include an indication of a measure of deviation (e.g., standard deviation) of the reference system distance which can be used to evaluate whether correction or manipulation is desirable. The reference system can also include one or more sets of tables that define the angular orientation of one or more dental features (e.g., an angular orientation of a tooth) with respect to one or more reference planes and a measure of deviation of the orientation. The planes and the dimensions between the planes of the reference framework can be determined as average or mean of a sample of two or more subjects (or of a larger population). The reference framework can include reference points or landmarks that correspond to facial and dental features of a subject that can be used for comparison to scale the reference system to the patient. For example, in accordance with some embodiments of the invention, the location of the centers of pupils of the eyes can be used as reference points for the framework and distance between the pupils can be used to scale the reference framework to the subject and some or all of the reference distances can be scaled according to the ratio of patient pupillary distance to the reference framework pupillary distance. An example of a framework according to some embodiments of the invention is shown in FIGS. 5-8.

According to some embodiments of the invention, still images of the subject can be taken and used to produce a three dimensional representation of the subject (e.g., at least the dental features to be evaluated). The images can include images of the subject's face and head as well as images of impressions of the subject's teeth. After scaling the reference framework for the subject, the reference framework can be overlaid onto the images of the subject for comparison and to enable the development of a treatment plan. The differences between the location and orientation of the subject's dental features (e.g., teeth, upper and lower jaws) and the reference system can be evaluated on a feature by feature basis to determine whether it is desirable to manipulate a particular feature. The reference system can include an identification of a measure of deviation for the standard as a whole and/or for some or all the dental features in order to assist an orthodontist in determining whether to manipulate a dental feature. For example, where a tooth position or orientation is less than the measure of deviation (e.g., one standard deviation), the tooth may not need to be manipulated.

In accordance with some embodiments of the invention, a computer system can be used to assist an orthodontist with evaluating a subject's need for treatment. In accordance with some embodiments of the invention, the computer system can include a personal computer such as well-known Microsoft Windows™, Apple MacIntosh™ or Linux based personal computers. The computer system can include a processor and associated volatile and non-volatile memory storing computer programs and data. These computer systems can be adapted to connect to local and wide area networks, including the Internet and can connect to peripheral devices, such as printers and image generating devices (e.g., cameras and x-ray imaging systems). The computer system can include software that processes images taken of a subject to create a 3D representation of the subject, such as a virtual 3D model of the subject. Either automatically, or with the assistance of an orthodontist (or an aide), the computer system can be used to identify the landmarks (e.g., the pupils) in the 3D representation (e.g., the 3D model can be updated) and this information can be used to scale the reference system framework to fit the subject (e.g., the 3D representation) using the reference measurements. The computer system can overlay the scaled reference system framework on the virtual 3D model of the subject to assist the orthodontist with evaluating the position and the orientation of the subject's teeth and comparing them to the reference planes of the framework. Where the subject's teeth deviate from the reference system by an excessive amount, the orthodontist can treat the subject, such as with braces or other orthodontic appliances.

During the course of treatment, the subject's teeth can be manipulated into new positions and orientations. In addition, during the course of treatment it is possible that the subject will grow. At intermediate points in time during the course of treatment, new images and/or impressions of the subject can be taken and a new 3D virtual model of the subject can be created. When a new 3D virtual model is created, the reference system can be rescaled to accommodate any changes (e.g. growth and/or treatment progress) in the subject. This enables the reference system to adapt to changes in the subject and continue to provide a useful standard over the course of treatment, even when the subject is growing.

In accordance with some embodiments, a reference standard can be created by evaluating one or more subjects thought to have desirable or aesthetically pleasing features. This can be accomplished by evaluating images of one or more potential subject or taking a survey of opinions. In accordance with some embodiments of the invention, face models including a number of females and/or males in a predefined age range can be orthodontically screened for ideal or otherwise desirable occlusion. Ideal or desirable occlusion can be defined by the following inclusion criteria: 1) less than 3 mm crowding or spacing. 2) No missing teeth other than the third molars, 3) Overjet between 1.5 and 3 mm, 4) Overbite between 1.5 and 3 mm, 5) Class I canine and molar relationships (+/−1.5 mm), and 6) CR-CO discrepancy less than 1 mm. All models that satisfied the orthodontic inclusion criteria can be photographed. In accordance with some embodiments, a set of three facial photographs can be taken: one photograph of the front and one photograph of each side of the face. In accordance with some embodiments, the photographs can include one smiling frontal shot, one frontal shot with the lips relaxed, and one profile shot from the right side. The facial photographs can be taken to conform with the standards of the American Board of Orthodontics (http://www.americanboardortho.com/professionals/clinicalexam/casereportpresentation/preparat ion/photos.aspx). The photographs can be taken at a relatively high resolution (e.g., 2560×1920) and included an area 3-4 inches around the head and down to the base of the neck. The photographs can be viewed by the evaluators at about one-quarter life size and in black and white to reduce distractions.

To minimize distractions, black and white images can be used and hair can be moved away from the face. The photographs of the orthodontically screened subgroup of the sample can be shown to a group of lay people to grade the model's faces based on facial attractiveness on a visual analogue scale and decide whether or not the faces were considered "acceptable" or desirable. The evaluators can be regular people (e.g., from the streets of a city, such as Boston or New York, etc.) and they can be offered something of value to compensate them for their time. Evaluators from professions that relate to facial aesthetics, such as people who work in the dental profession or any medical profession that involve working on the face can or should be excluded. Models that were considered to have acceptable profiles by a threshold number (e.g., 50%, 60%, 70%) of the evaluators and received an average visual analogue scale score greater than a predefined threshold score (e.g., 5.0, 5.5, 6.0, 6.5, 7.0, 7.5) can be selected to be part of the standard development.

In accordance with some embodiments of the invention, each of the selected models can have images of each of the teeth created. This can be accomplished by taking an impression of all the model's teeth and then digitizing (by taking one or more photographs) of the dental casts produced by the impression molds. Alternatively, each of the model's upper and lower teeth can be scanned, as well as a bite registration taken using, for example, an oral scanning system such as a Lava Chair-side Oral Scanner (3M ESPE, Maplewood, Minn.). Before the scanning, the subjects can be checked again for the dental exclusion criteria. A leaf gauge can be used to check centric relations. In accordance with some embodiments, none of the subjects included in the study can have a CR-CO discrepancy greater than 1 mm. The 3D facial scans of the patient's face can be done in natural head position (e.g., having the patient look at the horizon or themselves in a mirror) with the teeth together and the lips at rest using the Vectra M3 imaging system (Canfield Scientific, Fairfield, N.J.). This can be repeated with a full smile identified by visible premolars and changes to the contour of the eyes. The two facial scans, the bite registration, and both arches can be imported into imaging software, such as a customized beta version of Mirror (Canfield Scientific, Fairfield, N.J.). The 3D dental casts can be digitized with landmarks described by Huanca Ghislanzoni L T et al. [45]. FIG. 1 and table 1 show examples of the dental landmarks that can be identified and their descriptions according to some embodiments of the invention.

As shown in FIG. 1, the central incisors, canines, first premolars and first molars all have their mesial and distal contact points marked. The facial axis of the clinical crown (FACC) can be marked as described by Andrews [46] as the line passing through the most prominent part of the incisors, canines, and premolars. On the molars, the FACC line can be identified as the line passing through the most prominent buccal groove. [46] A similar line can be marked on the lingual/palatal grooves of the molars and identified as the lingual FACC. [45] The occlusal and gingival limits of the FACC can also be marked. On the incisors, canines and premolars the FACC line can be extended to the palatal and its intersection with the lingual/palatal gingiva can be marked. On the molars, the intersection of the lingual/palatal FACC and the lingual/palatal gingival margin can be marked. The FA point can be marked at the middle of the FACC line and a tangent to it can be identified. The long axis of the clinical crown can be identified as a line connecting the incisal edge (canine ridge extension of the FACC line for canines) and point midway between the labial and lingual/palatal gingival extensions of the FACC line. On the premolars and molars, a point marking the intersection of a line connecting the mesial and distal contact points and the FACC can be used instead of the incisal limit of the FACC line. Table 2 describes the dental lines that can be used in the development of a reference standard according to some embodiments of the invention.

The facial landmarks can be identified as described by Plooij et al. [20] and Farkas et al. [47]. Table 3 defines the facial landmarks used in this embodiment and FIGS. 2-8 show some of the landmarks that can be used in the development of a reference standard according to some embodiments of the invention. All midline landmarks can be first located using the sagittal view and transversely adjusted to be on the midline using a frontal view of the face. Lateral landmarks can be identified using at least two different image views to insure accurate positioning.

Figure 2:
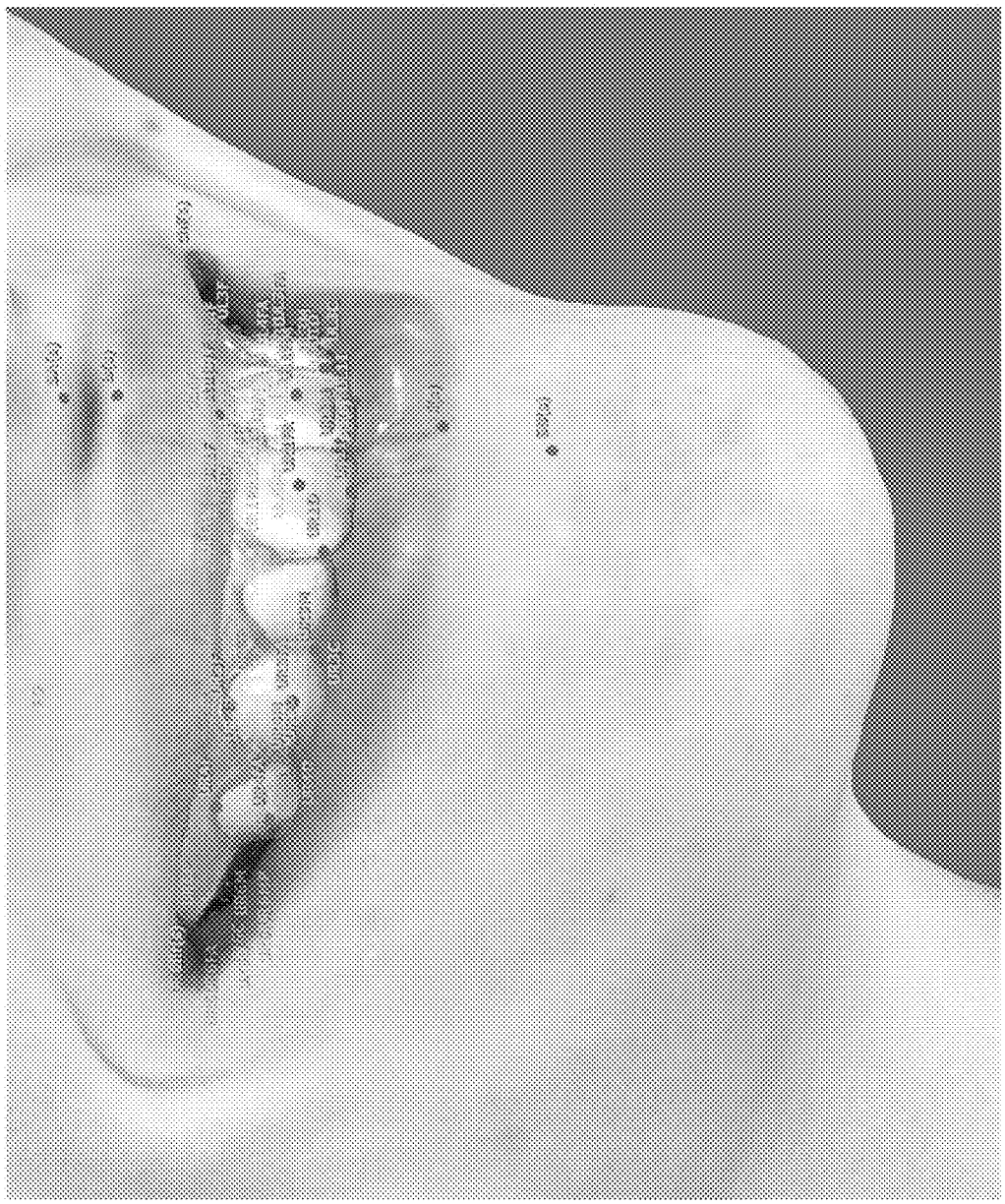
FIG. 2 shows a smiling facial image of a patient showing dental and facial landmarks according to some embodiments of the invention.

The mandibular teeth can be indexed to the maxillary teeth using the bite registration. The maxillary teeth can be indexed to the smiling 3D facial image using the incisal and gingival embrasures of the anterior teeth as shown in FIG. 2.

Figure 3:
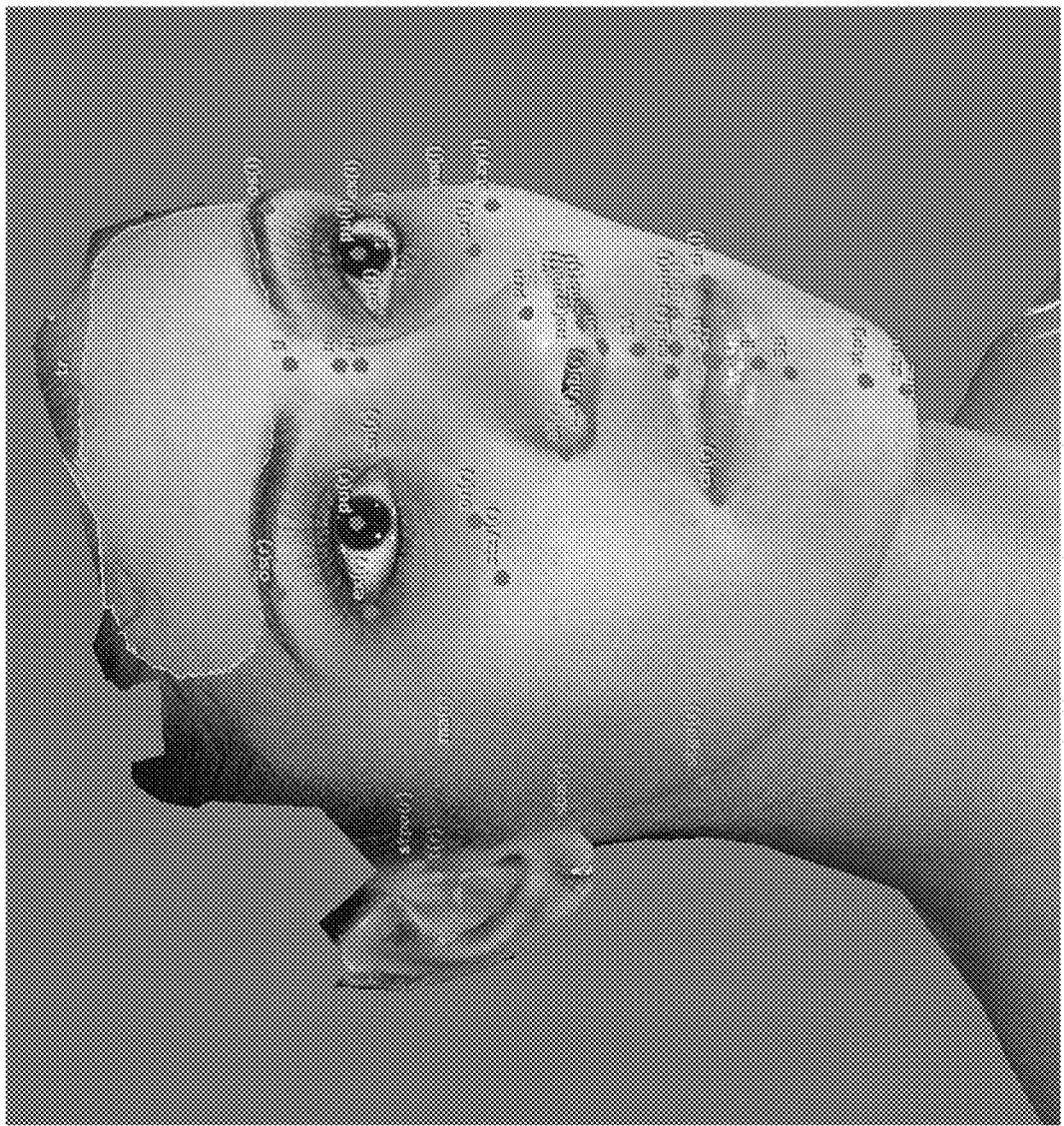
FIG. 3 shows a non-smiling facial image of a patient showing dental and facial landmarks according to some embodiments of the invention.

The smiling and non-smiling 3D facial images can be indexed using the curvature of the forehead as shown in FIG. 3. Customized software can be used to enable a user to mark an area on the non-smiling face and to search the smiling image for substantially the same curvature and then register the two images. This process can be used with other facial features that, like the forehead contour, do not change when the patient smiles. In accordance with some embodiments of the invention, other facial features such as features of the eye brows and/or the forehead can be used as reference points. A paintbrush tool can be used to select the area between the hairline and the eyebrows. That forehead area can be marked on the 3D photograph at rest. A "register on surface" command can be used to find the same or similar curvature on a smiling face and superimpose the two images by registering the matching curvatures of the forehead.

Figure 4:
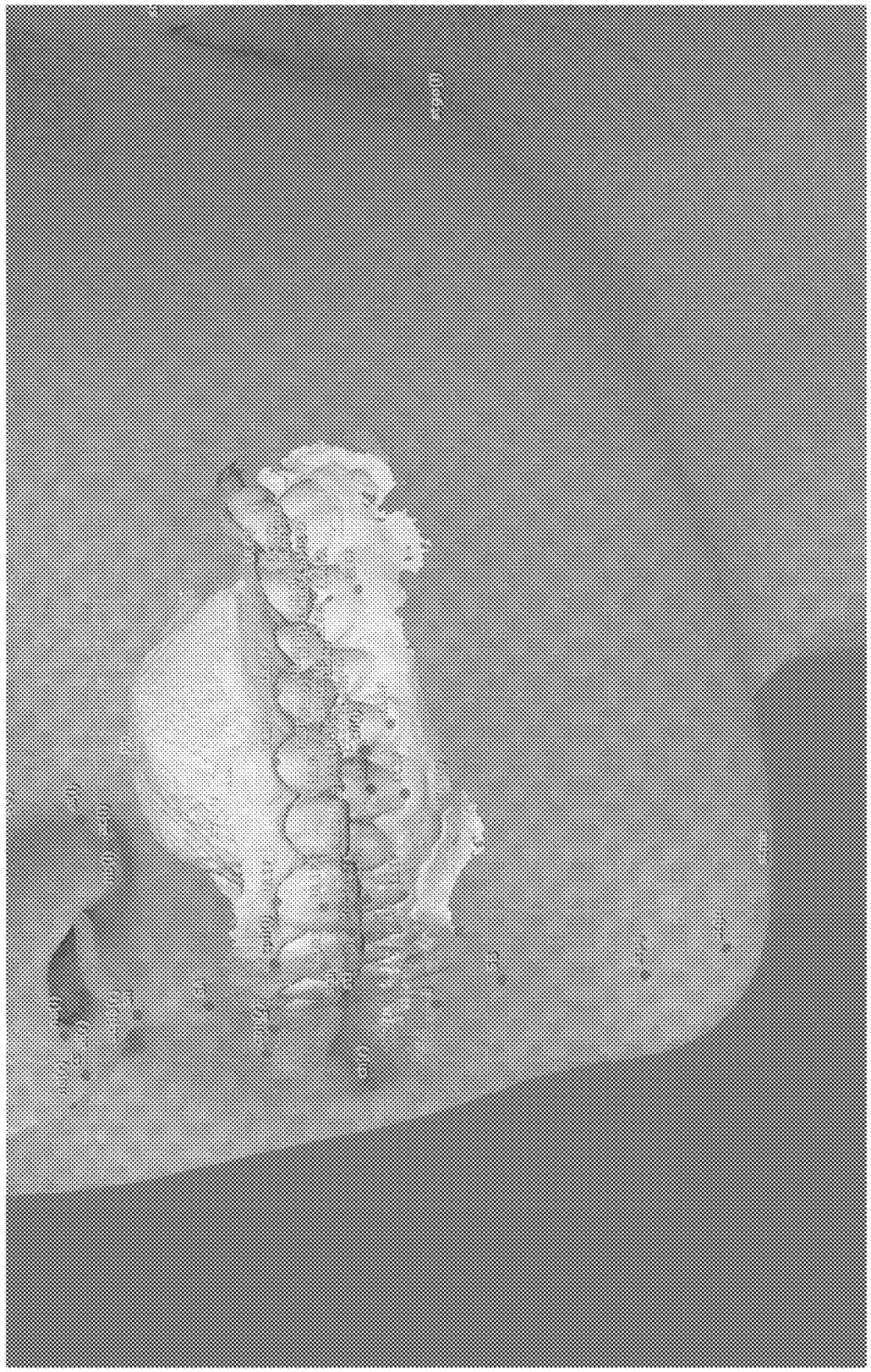
FIG. 4 shows a facial image combined with images of maxillary and mandibular teeth forming a 3D representation according to some embodiments of the invention.

Using the software, all the different component images can be indexed to each other and their coordinates can be identified relative to the (0,0,0) point located midway between the pupils, the m point, shown in FIG. 3. Any one of the five component images could be made invisible or transparent to better view a particular structure or group of structures. FIG. 4 shows the maxillary and mandibular teeth indexed to the relaxed-lip 3D image of the face after being registered using the smiling 3D image. As shown in FIG. 4, the face with the smile can be made invisible and the face with the lips relaxed can be made transparent to make it possible to view the orientation of the maxillary and mandibular teeth.

Figure 5:
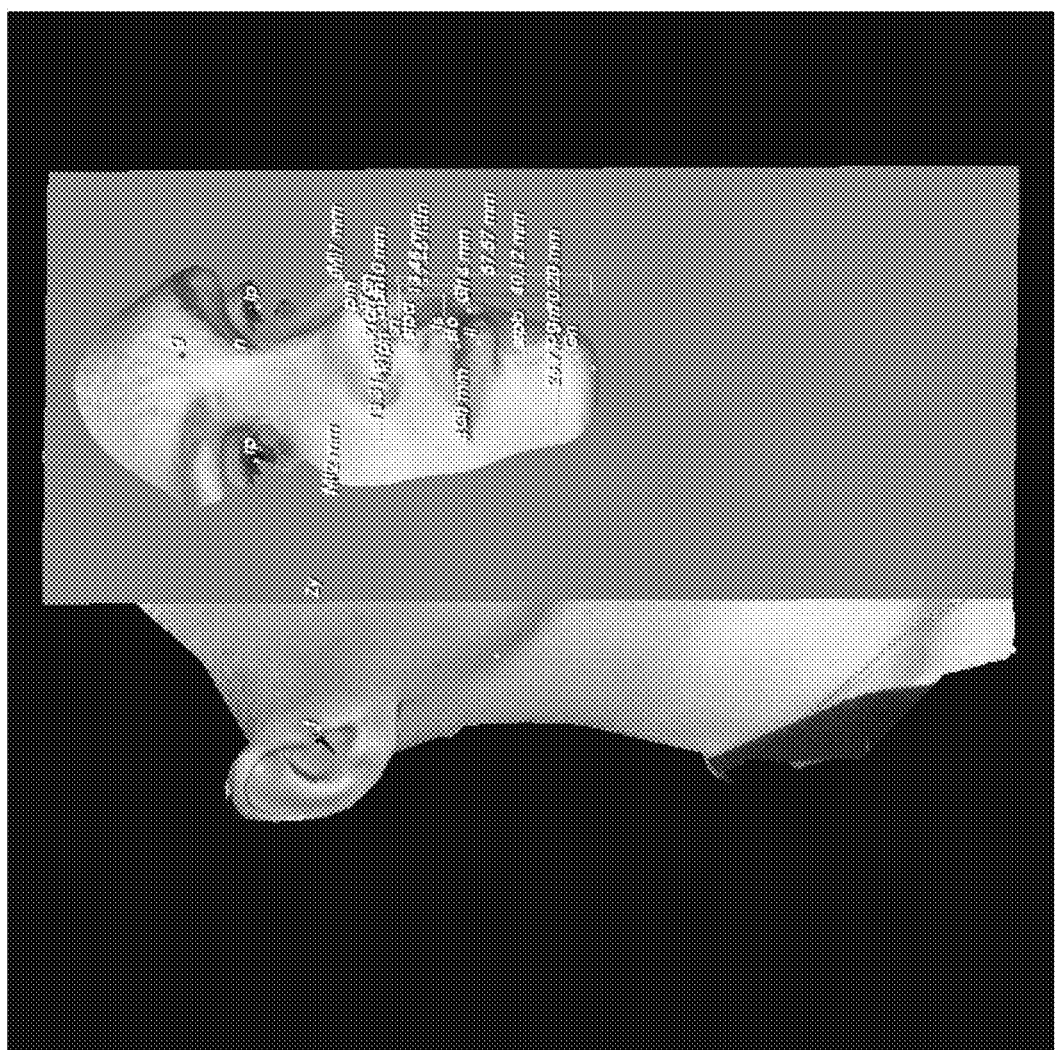
FIG. 5 shows a non-smiling facial image of a patient showing dental and facial landmarks and the mid-coronal (MC) plane according to some embodiments of the invention.
Figure 6:
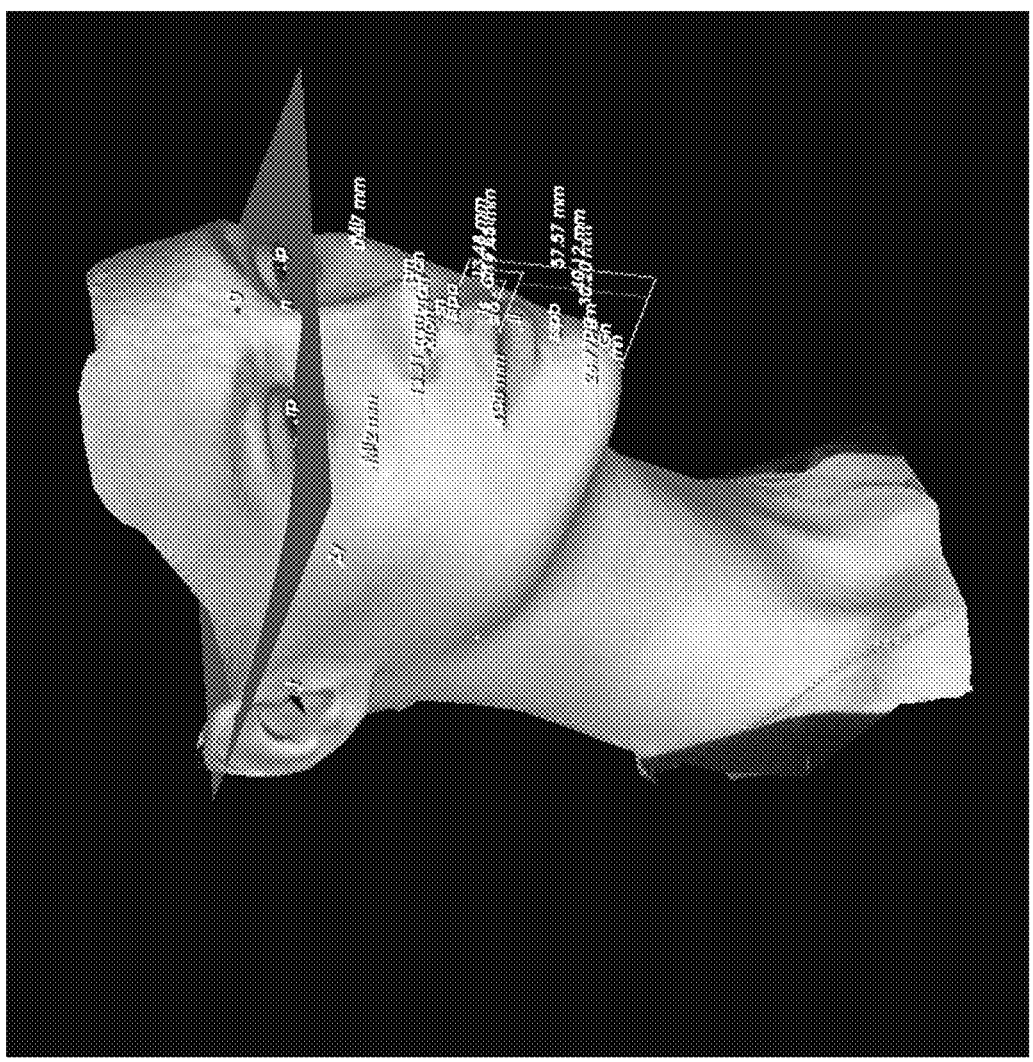
FIG. 6 shows a non-smiling facial image of a patient showing dental and facial landmarks and the mid-axial (MA) plane according to some embodiments of the invention.
Figure 7:
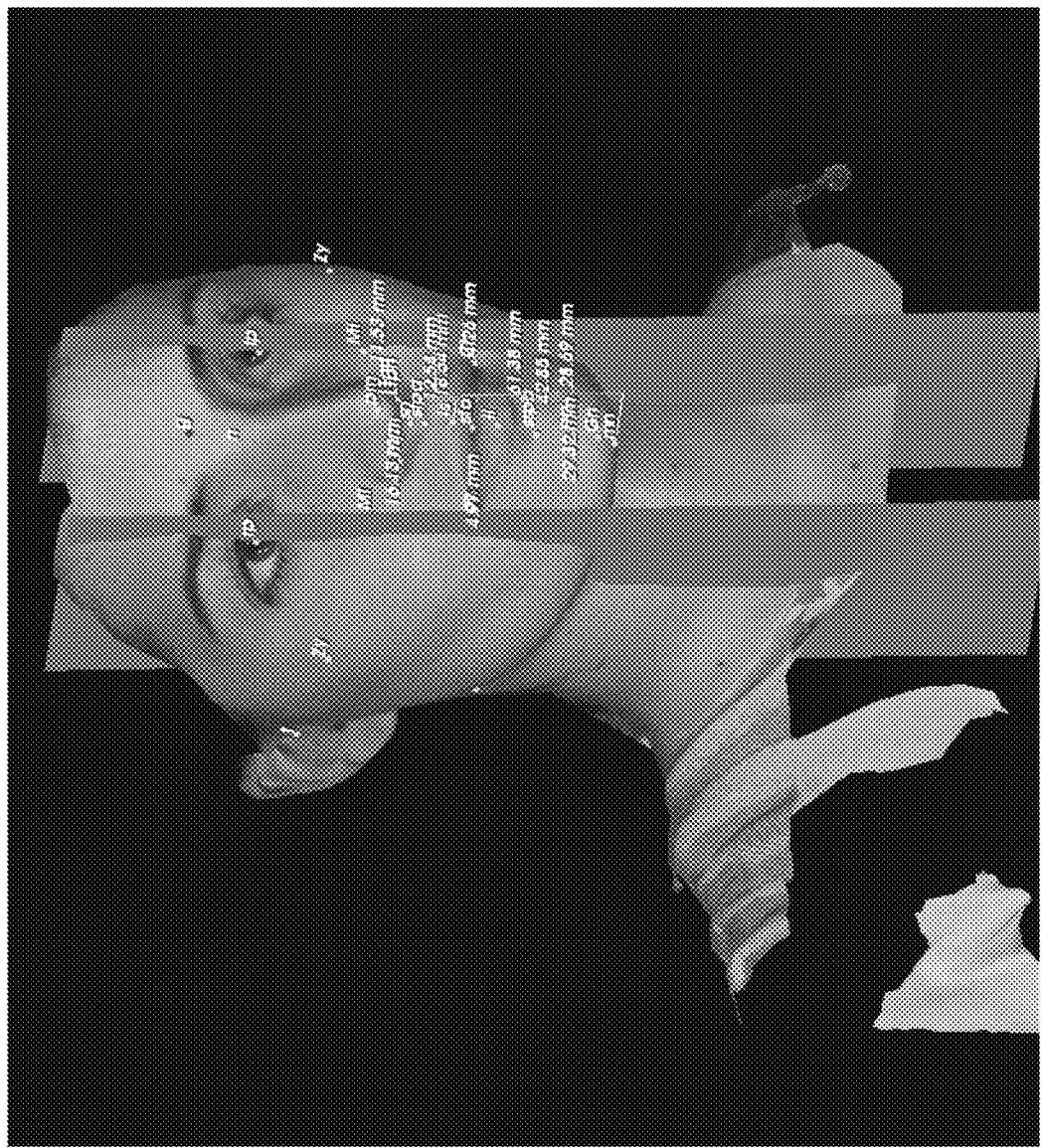
FIG. 7 shows a non-smiling facial image of a patient showing dental and facial landmarks, the right mid-sagittal (rtMS) plane and the left mid-sagittal (ltMS) plane according to some embodiments of the invention.
Figure 8:
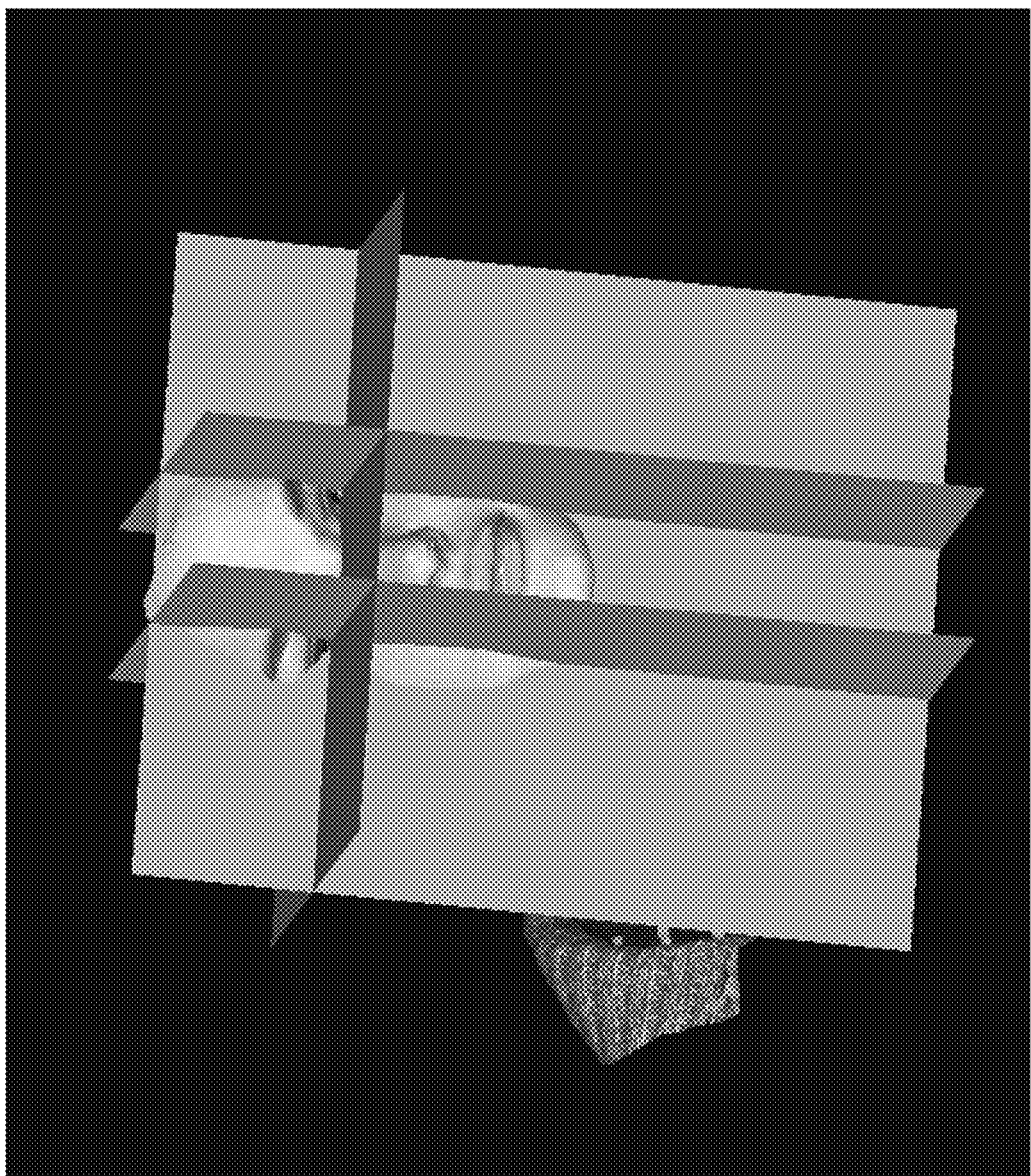
FIG. 8 shows a non-smiling facial image of a patient showing the MC plane, the MA plane, the rtMS plane and ltMS plane according to some embodiments of the invention.

Instead of using intracranial reference points, a mid-coronal plane, the MC-Plane, going through the centers of the pupils, perpendicular to the true Horizontal and determined by the patient's natural head position can be defined. The MC-Plane can be used as a reference for determining the anterioposterior position and orientation of facial and dental landmarks as shown in FIG. 5. In accordance with some embodiments, a mid-sagittal plane (MS-Plane) going through the m point (midway between the pupils) can be used as references to determine the transverse position and orientation of the facial and dental landmarks as well the inclination of the canines, premolars and molars. In accordance with some embodiments, as shown in FIG. 7, two sagittal planes through the right and left pupils perpendicular to the true horizontal plane (rtMS-plane, and ltMSplane), in addition to or instead of the mid-sagittal plane (MS-Plane), can be used as references to determine the transverse position and orientation of the facial and dental landmarks as well the inclination of the canines, premolars and molars. These planes can also be used to measure the transverse orientation of the occlusal plane and the mandibular plane. As shown in FIG. 6, an axial plane parallel to the true horizontal and passing through the pupils (MA-plane) can be used to determine the vertical position and orientation of the facial and dental landmarks, the inclination of the incisors, the A-P inclination of the occlusal plane, and the A-P inclination of mandibular plane. In accordance with some embodiments of the invention, FIG. 8 shows four of the 5 reference planes (the MS-plane omitted for clarity) used to define the reference system. According to some embodiments of the invention, Table 4 describes each of the planes that can be used to develop the reference standard. The measurements can be determined using the Mirror computer software or other 3D measuring tools.

In accordance with some embodiments of the invention, some or all of the records can be digitized and measured. The dentofacial images that were orthodontically screened and selected by the public for attractiveness can be averaged, for example, using a General Procustes Analysis to determine the average or mean location of each landmark, after eliminating variations in size, translation, and rotation. [48] [49] In addition, deviation or acceptable range values can also be determined, for example, by determining standard deviations for the records. The average or mean location of each landmark and the standard deviation can be compiled into a table or a computer table or data base and used as part of the reference system for evaluating subsequent patients.

Diagnosis

The present invention is directed to a method and system for orthodontic diagnosis and treatment planning without using radiographic exposure beyond what would be necessary for general dental evaluation. The image records can be supplemented with additional image records as determined by the orthodontist's assessment of the case. If a patient has an impacted tooth or questionable bone support for example, a Cone Beam Computed Tomography (CBCT) image limited to that area of interest can be taken at the orthodontist's discretion. Similarly, a CBCT limited to the area of interest can be taken for joint imaging (hard or soft tissue), airway assessment, sleep studies, and the temporomandibular joint.

In accordance with the invention, the reference system was developed to represent an orthodontic goal as guide for treatment of orthodontic patients. Orthodontic criteria were used in prescreening the models for desirable or standard dental conditions and relationships. The reference system measurements according to the invention can serve as a tool to measure how a patient deviates from a reference framework and to aid the orthodontist in making treatment decisions.

In accordance with some embodiments of the invention, an orthodontic patient can have images of each of the teeth created. This can be accomplished by taking an impression of all the patient's teeth and then digitizing (by taking one or more photographs) of the dental casts produced by the impression molds. Alternatively, each of the patient's upper and lower teeth can be scanned, as well as a bite registration taken using a Lava Chair-side Oral Scanner (3M ESPE, Maplewood, Minn.). In addition, 3D facial scans of the patient's face can be done in natural head position with the teeth together and the lips at rest using the Vectra M3 imaging system (Canfield Scientific, Fairfield, N.J.). This can be repeated with a full smile identified by visible premolars and changes to the contour of the eyes. The two facial scans, the bite registration, and both arches can be imported into imaging software, such as a customized beta version of Mirror (Canfield Scientific, Fairfield, N.J.). The 3D dental casts can be digitized with landmarks described by Huanca Ghislanzoni L T et al. [45]

As a result, a set of images or a 3D virtual representation of the orthodontic patient, similar to FIGS. 1-4 can be created. In accordance with some embodiments of the invention a full 3D virtual representation of the patient can be produced. In accordance with some embodiments of the invention, a plurality of images of the patient can be produced, for example, providing a frontal image perpendicular to the MC Plane and side images perpendicular to the sagittal planes (e.g., rtMS plane and ltMS plane). Additional views can also be created. In accordance with embodiments, a view of each tooth to be manipulated can be created.

In accordance with some embodiments of the invention, the reference planes can be defined in the 3D representation of the patient and the position and/or orientation measurements for one or more landmarks on one or more dental or facial features can be determined. These measurements can be determined in the same way as the measurements were determined in developing the reference standard values of the reference system.

In accordance with some embodiments of the invention, an orthodontic patient's measurements can be compared to the Mean values and standard deviations for the different dentofacial measurements from reference system, for example, the values provided in Tables 5, 6 and 7. The information from the Tables can be used to determine the location, amount, and direction of a patient's dental and facial discrepancies. The reference standard along with the initial measurements can then be used for treatment planning as well as evaluating progress and treatment outcomes. For example, a patient with upper and lower incisor and lip measurements that indicate protrusion relative to the MC-Plane may not be suitable for additional proclination to relieve moderate to severe dental crowding and vice versa. A patient with a posterior lingual cross-bite and upper molars that are labially inclined relative to the MS-Plane may require skeletal expansion instead of dentally widening the arches. The alar curvature can be used as an indicator of maxillary position and soft tissue pogonion can be used to indicate mandibular position. Both of those landmarks are not influenced by the position of the teeth and would give a better indication of skeletal relationships than soft tissue A point and B point. A facial scan with a centric relation jig can be used to ensure correct condylar position. The angle between the plane connecting the pupils to the alar bases and the plane connecting the pupils to soft tissue pogonion can be used to determine whether or not the patient has a normal skeletal relationship. The degree of discrepancy in distance and angle of each of the jaws relative to the MC-plane can be used in deciding which jaw is at fault. Additional radiographic exposure may be necessary to visualize the maxilla and mandible when planning orthognathic surgery, but the conclusion that orthognathic surgery is necessary can be reached without radiographic exposure of the cranium. Orthognathic surgery can be reserved for the treatment of patients with severe skeletal discrepancies which represent a small segment of the population[50].

In accordance with some embodiments of the invention, the patient's dentofacial images in a natural head position can be overlaid onto or with a template that has been developed according to the reference standard. In accordance with the invention, the template can be scaled using the pupillary distances and registered to the 3D representation of the patient using the pupils as landmarks. According to some embodiments of the invention, the location and degree of discrepancy can then be visually evaluated and described. According to some embodiments of the invention a 3D virtual representation of the patient can be compared using computer software to the scaled and registered template to determine differences in 3D space.

Figure 10:
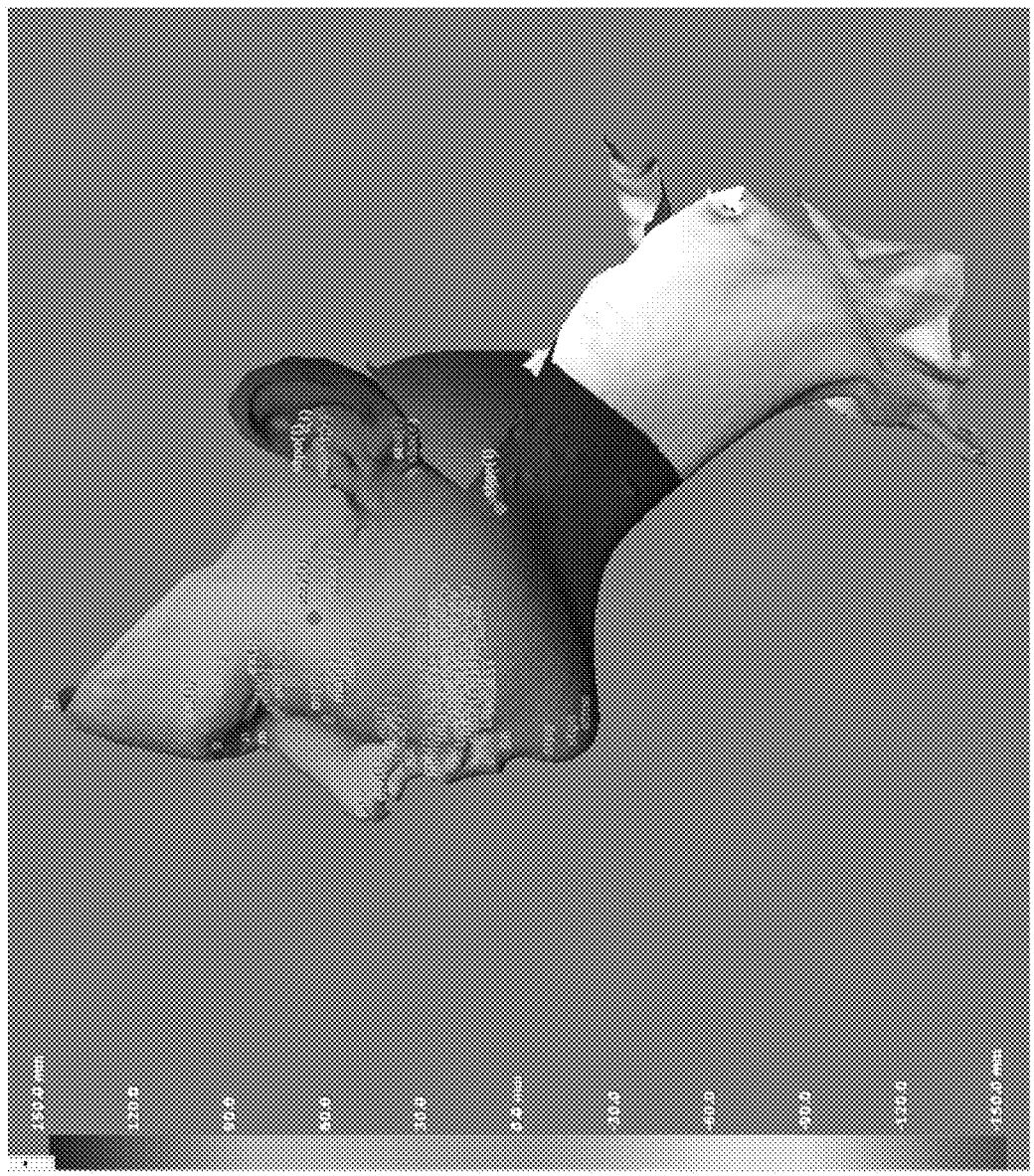
FIG. 10 shows a color map diagram side view of a subject according to some embodiments of the invention.

In accordance with some embodiments of the invention, the patients' images can also be warped to the standard and the different components of the dentofacial image can be color mapped to show deviations. The warping eliminates size differences and highlights shape differences. In accordance with some embodiments of the invention, FIG. 10 shows the face of one subject along with color mapping that shows how most of her face conforms to the reference standard. The green areas of the subject shown in FIG. 10 indicate surfaces that correspond closely to the reference standard, whereas the blue areas correspond to surfaces that are slightly forward or anterior of the reference standard.

Figure 11:
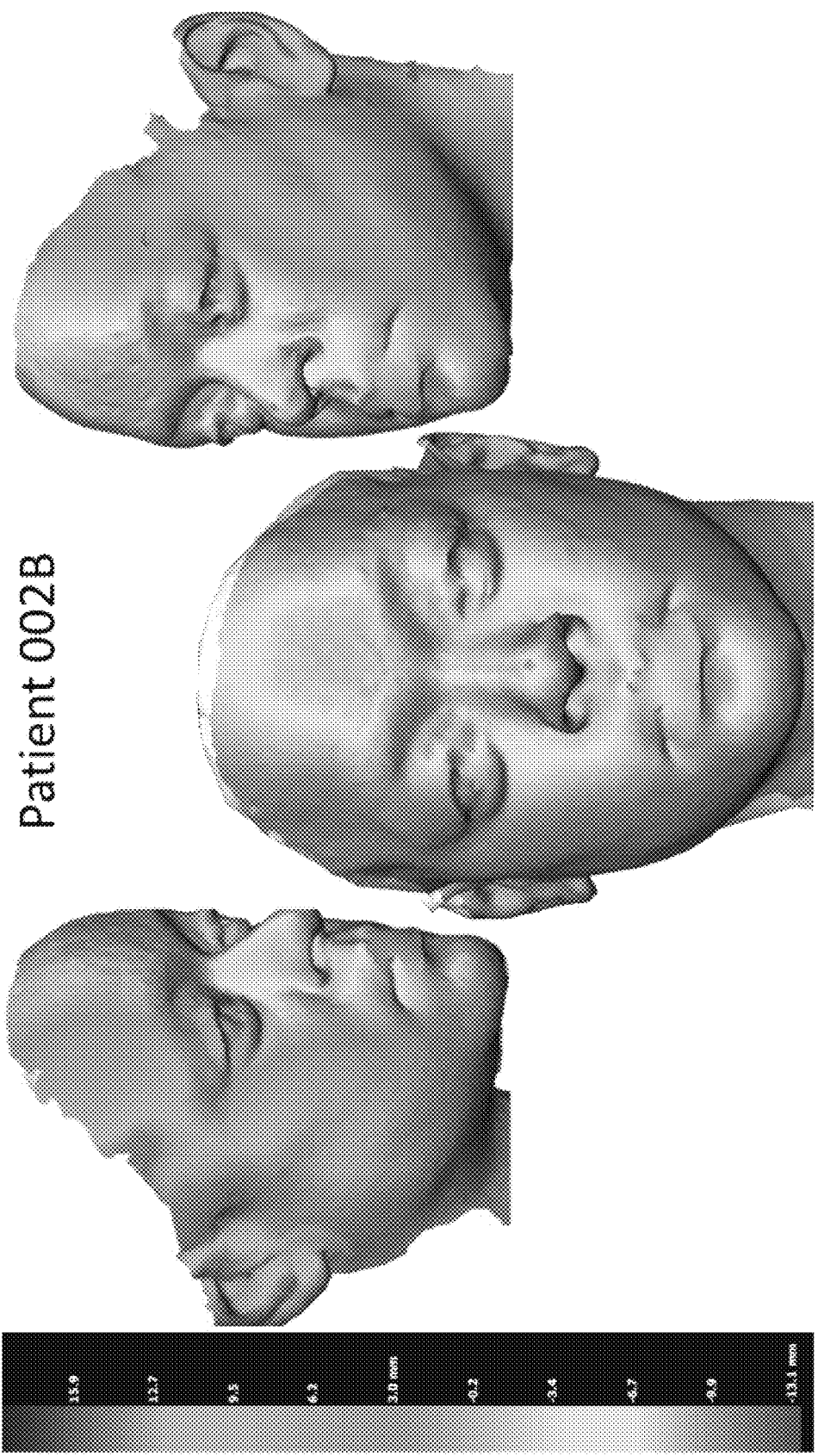
FIG. 11 shows a color map diagram of a patient according to some embodiments of the invention.
Figure 12:
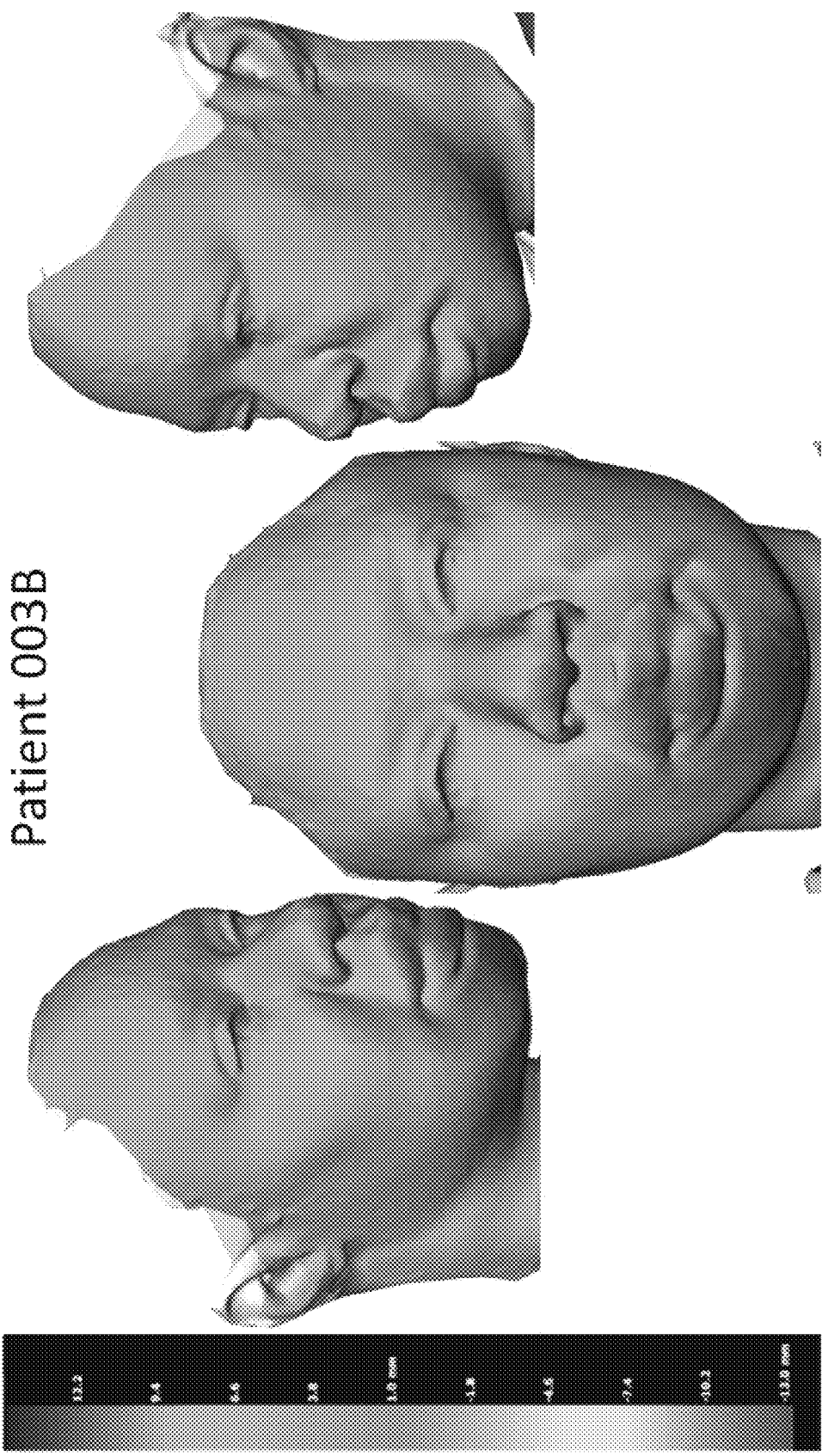
FIG. 12 shows a color map diagram of a patient according to some embodiments of the invention.

In accordance with some embodiments of the invention, FIGS. 11 and 12 show the faces and teeth of two orthodontic patients with color mapping that represents their deviations from the reference standard. While the green areas of the subject shown in FIG. 11 illuminate the surfaces that correspond closely to the reference standard, the yellow areas correspond to facial features and surfaces that are slightly behind or posterior of the reference standard. In contrast, as shown in FIG. 12, blue areas correspond to facial features that are slightly forward or anterior of the reference standard. These images can be used by an orthodontist to identify underlying dental features that may need adjustment. This information, in combination with the landmark discrepancy data, can be used to assist an orthodontist with the preparation of a treatment plan for each patient.

Figure 13:
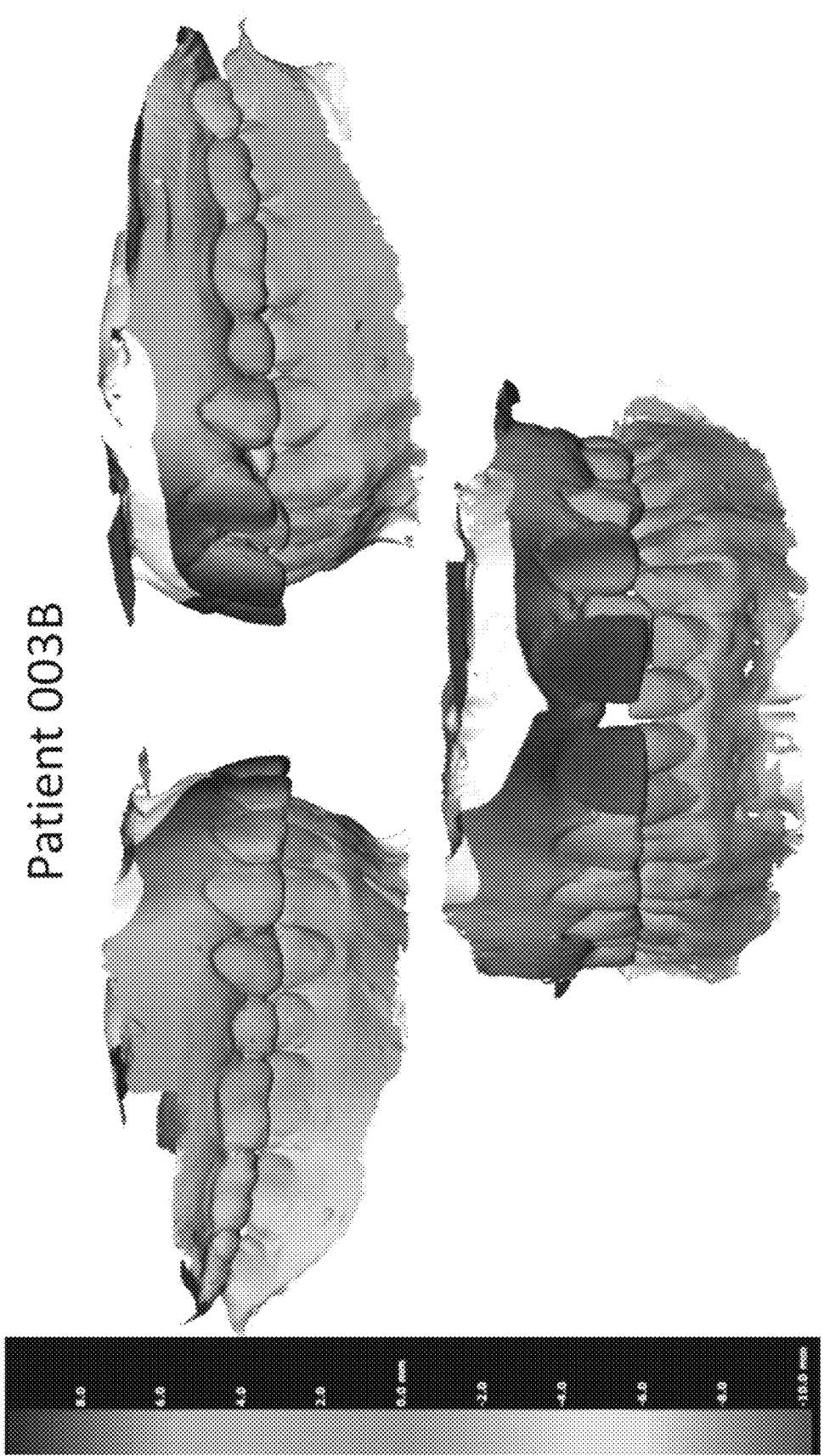
FIG. 13 shows a color map diagram of a patient according to some embodiments of the invention.

In accordance with some embodiments of the invention, FIG. 13 shows the teeth of an orthodontic patient with upper centrals and canines that are ahead of the standard (e.g., highlighted in blue) and a palatally displaced upper left lateral that matches the standard (e.g. highlighted in green).

A patient's initial template (e.g., 3D representation or 3D virtual model) can similarly be used to evaluate changes that have occurred as a result of growth and/or treatment. In accordance with some embodiments, the subsequent 3D representation or 3D virtual model can be developed from subsequent images and compared with a prior or the initial 3D representation or virtual model of the patient to determined and evaluate changes that have occurred due to growth and/or treatment. This can help an orthodontist evaluate the effectiveness of treatment and indicate possible changes to treatment. In accordance with some embodiments of the invention, Dental changes during treatment can be assessed by superimposing current and prior 3D representations or 3D virtual models on the palatal rugae which have been shown to be individually unique and stable structures[51].

In accordance with some embodiments of the invention, the orthodontist can use the differences between the patient's measurements and the reference system positional and orientational standards to assess the need for treatment on a feature by feature (e.g., tooth by tooth) basis. Further the differences or deviations from the reference standard can be evaluated against the reference standard deviation (e.g., a standard deviation) to determine a weight as to the need or requirement for treatment. For example, where a patient's difference is within one standard deviation for a location of a tooth, the need for treatment can be indicated as low, whereas is a patient's difference is greater than two standard deviations, need for treatment can indicated as higher. Where the orthodontist determines the need for treatment, braces or other orthodontic appliances can be installed to manipulate the dental features to achieve a desired outcome as part of a treatment plan.

Since the methods and system according to the invention use photographic imaging as opposed to x-ray imaging, it does not pose any risk to the patient and the records (images) can be retaken as frequently as the orthodontist feels necessary even if it is merely for documentation or evaluating outcomes with no direct benefit to the patient.

The methods and systems according to the invention use the eyes and the natural head position as a point of reference instead of the cranial base. Natural head position has been shown to be extremely reproducible and has been previously used as a reference for making cephalometric measurements. [5][6] Studies have shown that between the age of 5 and 19 the eyes experience less than 2 mm of growth [52][53] which is much less significant than the growth of the other parts of the face.

The methods and systems according to the invention can also be utilized for facial growth measurements since volumetric measurements and taking the records with a CR jig can determine whether sagittal correction is attributed to growth or mandibular posture.

Figure 14:
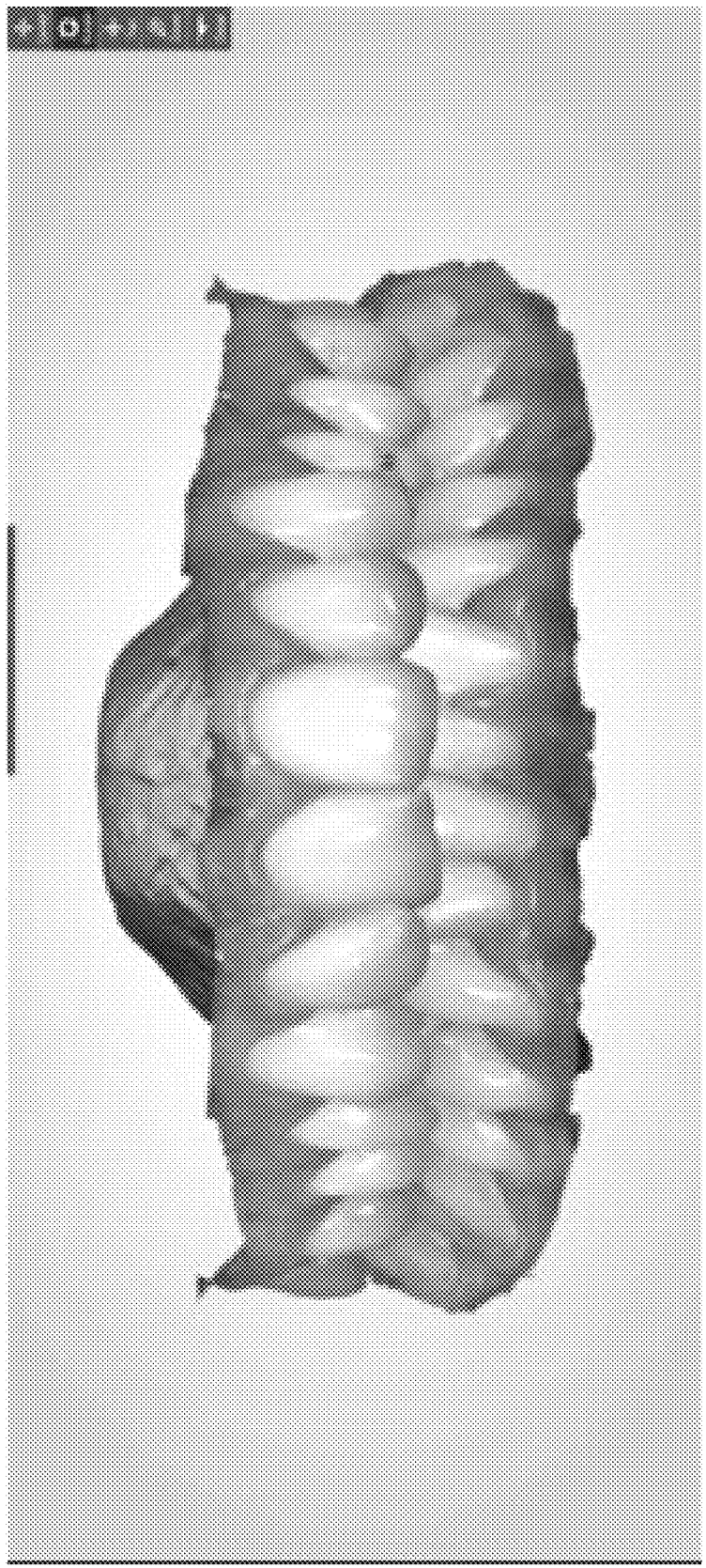
FIG. 14 shows a color 3D representation of the maxillary and mandibular teeth according to some embodiments of the invention.

In accordance with some embodiments of the invention, 3D dental imaging without color can be used to determine the average measurements and morphology for the subjects. In accordance with other embodiments of the invention, intraoral color scanners can be used to take the intraoral photographs of patients as well as the reference standard models as shown in FIG. 14.

In accordance with some embodiments of the invention, the orthodontist can catalogue all or some of the distance and angular measurements for a given patient in table or spreadsheet and then numerically analyze the table of data to determine the deviations or differences between the patient's measurements and the corresponding measurements, as shown in Tables 5-7. The numerical analysis can compare the patient deviation of a given measurement to the standard deviation for the corresponding measurement as indicated in Table 5-7. An abbreviated example is shown in Table 8. The numerical analysis can be used to identify those patient measurements that are greater than, for example, 1, 2 or 3 standard deviations as a way of highlighting those features (e.g., teeth or dental relationships) that should be considered for treatment.

In accordance with some embodiments, a computerized system can be used to perform some or all of this analysis. The computerize system can be used to store in memory and combine the images into a 3D representation of the patient's head and identify the landmarks and the reference planes, for example, by creating a 3D virtual scale model of the patients head. A clinician can review the computer created 3D virtual scale model of the patient's head to verify the correct location of the landmarks and the reference planes. The computer system can analyze the patient model data and determine the reference distances and reference angles with respect to the reference planes according to some or all the landmarks, angles and planes defined in Tables 1-4 and measurements. And Table 8 provides examples of analysis measurements that can be made using the patient model data and compared to reference standard measurement data shown in Tables 5-7. After the patient measurements are determined, the computer system can compare the patent measurement data to the reference standard data. Rules can be defined that flag individual patient measurements that deviate from the reference standard by a predefined amount or a predefined number of standard deviations. For example, a patient measurement that is greater than 1.5 standard deviations can be flagged in a display or highlighted in a different color. In addition, the computer system can use color maps such as those shown in FIGS. 10-13 to illustrate the deviation.

EXAMPLES

Figure 15:
FIGS. 15 and 16 show the smiling and relaxed facial views of the patient from FIG. 12 according to some embodiments of the invention.
Figure 15:
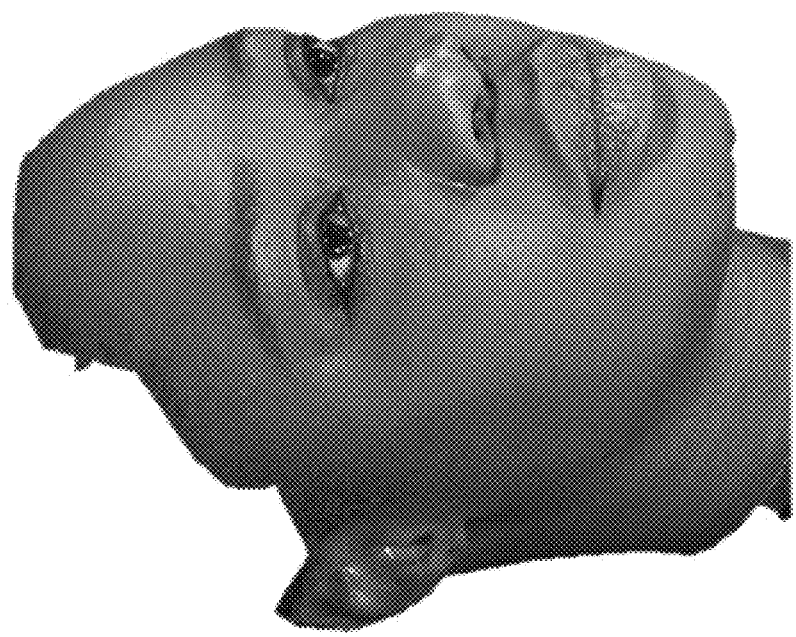
Figure 16:
Figure 16:
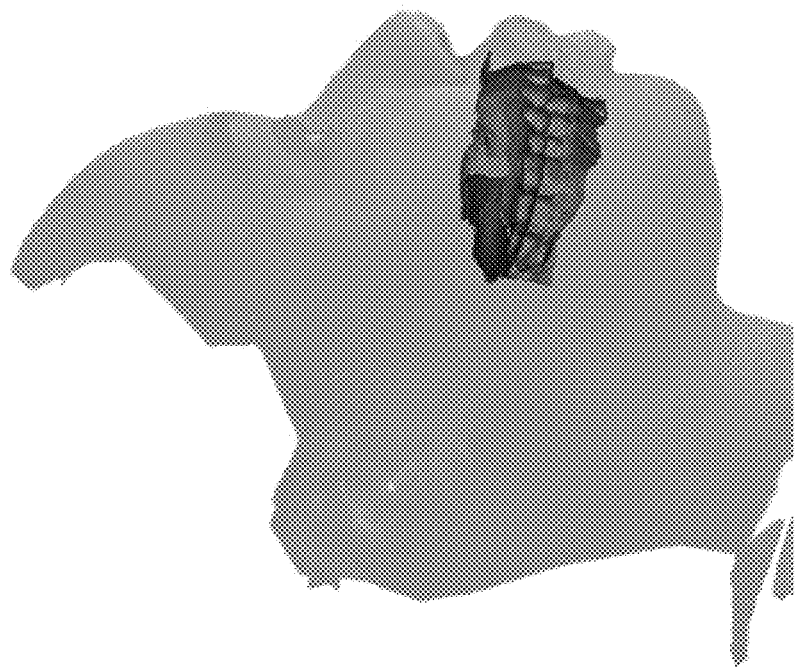

FIGS. 12, 15 and 16 show the face and teeth of an orthodontic patient with a palatally displaced upper left lateral and incisor buccal segments that are more class II on the left side. Table 8A shows an example of an analysis comparing the patient's values to the reference standard values. The comparison shows that the patient has slightly protrusive upper and lower jaws with average vertical and transverse relationships. For example, the Maxillary Lip Position was 3.7 standard deviations greater than the norm. The upper incisors are two standard deviations greater than the standard and the lower incisors are only one standard deviation more proclined than the standard. This is indicated by Maxillary Incisors (distance and angle) being 2.8 and 2.1 times the standard deviation from the norm, respectively. In accordance with some embodiments of the invention, an orthodontist could seek to treat this condition, for example, by extracting the first upper premolars to reduce the protrusion of the upper incisors. Additional treatment could be provided by braces to manipulate the position of the remaining teeth after the extraction. Braces and wires can then be used to relieve the crowding and retract the teeth into the extraction spaces. If the teeth were brought into alignment without extractions in this case the teeth would end up in a position that is more forward than the reference standard and would likely be considered less esthetically pleasing by most lay people. The lower teeth were only one standard deviation above the standard. Some orthodontists wanted to normalize their position as well and choose to extract upper and lower premolars. This would allow the orthodontist to normalize the angulation and position of the lower incisors and allow the upper incisors to be retracted even more. The degree to which a patient's values are brought closer to the reference standard often depends on the patient's wishes as well as a cost-risk-benefit consultation with the patient.

In one example, 175 females between the ages of 18 and 35 were orthodontically screened for ideal occlusion. This was defined by the following inclusion criteria: 1) less than 3 mm crowding or spacing. 2) No missing teeth other than the third molars, 3) Overjet between 1.5 and 3 mm, 4) Overbite between 1.5 and 3 mm, 5) Class I canine and molar relationships (+/−1.5 mm), and 6) CR-CO discrepancy less than 1 mm. All models that satisfied the orthodontic inclusion criteria had 3 standard facial photographs taken. To minimize distractions, black and white images were used and hair was moved away from the face. The photographs of the orthodontically screened subgroup of the sample were shown to a group of 41 lay people (21 females and 20 males) to grade the faces based on facial attractiveness on a visual analogue scale and decide whether or not the faces were considered "acceptable". The evaluators were regular people on the streets of Boston that were offered a 10 dollar gift card to compensate them for their time. The only exclusion criterion for evaluators was being from the dental profession or any medical profession that worked on the face. Subjects that were considered to have acceptable profiles by 60% of the evaluators and received an average visual analogue scale score greater than 5.8 were selected to be part of the standard. Each of the selected models had their upper and lower teeth scanned, as well as a bite registration using a Lava Chair-side Oral Scanner (3M ESPE, Maplewood, Minn.). Before the scanning, the subjects were checked again for the dental exclusion criteria. A leaf gauge was used to check centric relations. None of the subjects included in the study had a CR-CO discrepancy greater than 1 mm. The 3D facial scans were done in natural head position with the teeth together and the lips at rest using the Vectra M3 imaging system (Canfield Scientific, Fairfield, N.J.). This was then repeated with a full smile identified by visible premolars and changes to the contour of the eyes. The two facial scans, the bite registration, and both arches were imported into a customized beta version of Mirror (Canfield Scientific, Fairfield, N.J.). The 3D dental casts digitized with landmarks are described by Huanca Ghislanzoni L T et al. [45] FIG. 1 and table 1 provide examples of the dental landmarks that were identified and their descriptions.

The central incisors, canines, first premolars and first molars all had their mesial and distal contact points marked. The facial axis of the clinical crown (FACC) was marked as described by Andrews as the line passing through the most prominent part of the incisors, canines, and premolars. [46] On the molars the FACC line was identified as the line passing through the most prominent buccal groove. [46] A similar line was marked on the lingual/palatal grooves of the molars and identified as the lingual FACC. [45] The occlusal and gingival limits of the FACC were marked. On the incisors, canines and premolars, the FACC line was extended to the palatal and its intersection with the lingual/palatal gingiva was marked. On the molars the intersection of the lingual/palatal FACC and the lingual/palatal gingival margin was marked. The FA point was marked at the middle of the FACC line and a tangent to it was identified. The long axis of the clinical crown was identified as a line connecting the incisal edge (canine ridge extension of the FACC line for canines) and point midway between the labial and lingual/palatal gingival extensions of the FACC line. On the premolars and molars, a point marking the intersection of a line connecting the mesial and distal contact points and the FACC was used instead of the incisal limit of the FACC line. Table 2 describes the dental lines used in the analysis.

The facial landmarks were identified as described by Plooij et al. [20] and Farkas et al. [47] Table 3 defines the facial landmarks used in the study and FIGS. 2-8 show some of the landmarks that were used in the analysis. All midline landmarks were first located using the sagittal view and transversely adjusted to be on the midline using a frontal view of the face. Lateral landmarks were identified using at least two different views to insure accurate positioning.

The mandibular teeth were indexed to the maxillary teeth using the bite registration. The maxillary teeth were indexed to the smiling 3D facial image using the incisal and gingival embrasures of the anterior teeth (FIG. 2).

The smiling and non-smiling 3D facial images were indexed using curvature of the forehead. The customized software allowed the clinician to mark an area on the non-smiling face and it would search the smiling image for the same curvature and register the two images (FIG. 3).

Thus all the different components were indexed to each other and their coordinates could be identified relative to the (0,0,0) point located midway between the pupil (m point). Any one of the five components could be made invisible or transparent to better view a particular structure or group of structures. FIG. 4 shows the maxillary and mandibular teeth indexed to the relaxed-lip 3D image of the face after being registered using the smiling 3D image. In this image, the face with the smile was made invisible and the face with the lips relaxed was made transparent to make it possible to view the orientation of the maxillary and mandibular teeth.

Instead of using intracranial reference points, a coronal plane going through the centers of the pupils and perpendicular to the true horizontal determined by the patient's natural head position. The MC-Plane was used as a reference for determining the anterioposterior position of facial and dental landmarks (FIG. 5). A mid sagittal plane (MS-Plane) going through the m point (midway between the pupils) and two sagittal planes through the right and left pupils perpendicular to the true horizontal plane (rtMS-plane, and ltMS-plane) were used as references to determine the transverse position of the facial and dental landmarks as well the inclination of the canines premolars and molars (FIG. 6). These planes were also used to measure the transverse orientation of the occlusal plane and the mandibular plane. An axial plane parallel to the true horizontal and passing through the pupils (MA-plane) was used to determine the vertical position of the facial and dental landmarks, the inclination of the incisors, the A-P inclination of the occlusal plane, and the A-P inclination of mandibular plane (FIG. 7). FIG. 8 shows four of the 5 reference planes used (The image was taken out of natural head position to make the planes more visible). Table 4 describes the planes used in the analysis. The measurements were all calculated using the custom version of the Mirror software.

In this example, 8 sets of records were digitized and measured by two different examiners twice, 7 days apart) to determine inter and intra-examiner error.

The dentofacial images that were orthodontically screened and selected by the public for attractiveness were averaged using a General Procustes Analysis to determine the average location of each landmark after eliminating variations in size, translation, and rotation. [48][49]

The protocol for this study was approved by an institutional review board. The face models were considered contractors and all the surveys were anonymous.

Results:

In this study, 21 of the 41 evaluators were female and 20 were male. Of the 20 male evaluators, 11 were Asian, 4 were Caucasians, 3 were African American, and 2 were Indian. The mean age for the male evaluators was 23.65 with a standard deviation of 4.9. Two of the males had graduate degrees, 7 had college degrees, 8 had completed high school, and 2 had diplomas. Of the 21 female evaluators, 10 were Caucasian, 5 were Hispanic, 3 were Asian, 2 were African American, and 1 was Indian. The average age of the female evaluators was 28.86 with a standard deviation of 3.95. One of the female evaluators had a graduate degree, 6 had college level educations, 7 had associate degrees or went to trade school, 5 had high school level educations, and 2 had dropped out after the $9^{th}$ grade.

Of the 170 female subjects screened, 60 satisfied the orthodontic inclusion criteria. A total of 34 females that satisfied the inclusion criteria were considered to have acceptable faces by over 60% of the evaluators and had an average visual analogue scale of 6 or higher. Four female subjects that had passed the initial screening were excluded upon closer examination of their teeth. One of the subjects was found to have a missing lower incisor. Two of them had a partial class II relationship on one side, and one of the subjects had a first molar in lingual cross-bite. Six models did not come for their imaging sessions so the final sample that made up the female standard included 24 subjects. They all identified themselves as Caucasian but when asked about their family background approximately 50% of the scanned models had one parent that was African America, or Hispanic, or Mediterranean. The mean age for the female models was 20.9 years with a standard deviation of 2.8 years.

Figure 9C:
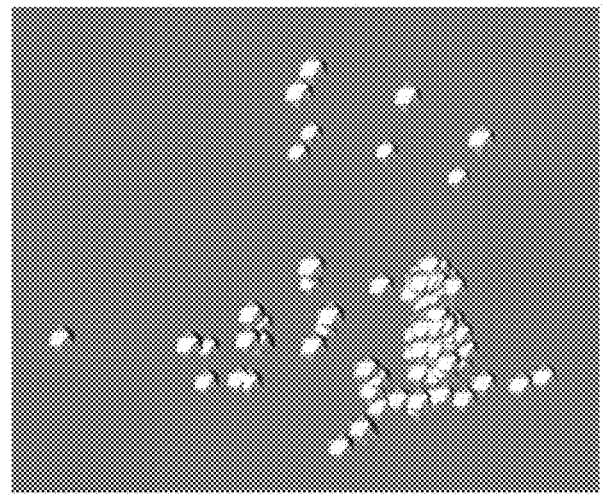
FIGS. 9A, 9B, and 9C show a diagrammatic views of the average locations of various facial and dental landmarks from the front, angled and side views, according to some embodiments of the invention.
Figure 9B:
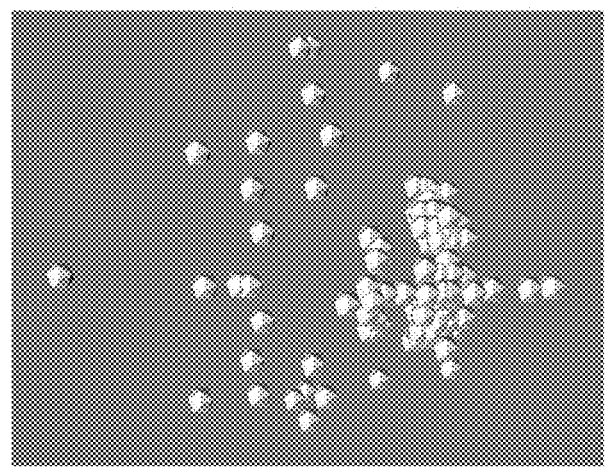
Figure 9A:
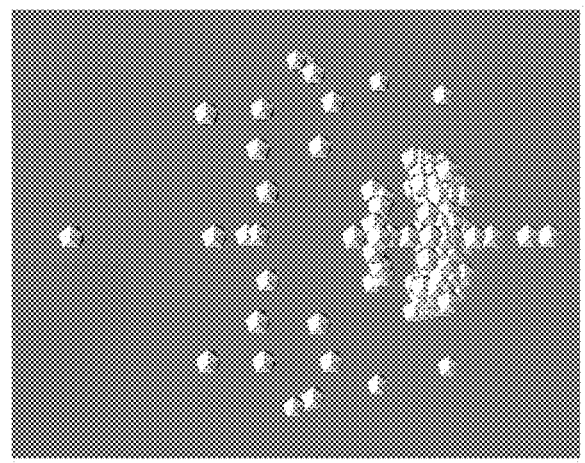

The selected faces had variation in size, location, and rotation eliminated using a General Procrustes Analyses. This resulted in a data set containing an average location of each of the identified landmarks. A diagrammatic representation of these landmarks is shown in FIGS. 9A (a front view), 9B (an angled view), and 9C (as side view).

A custom analysis was developed to utilize the reference planes described above to measure the position and orientation of different dentofacial structures. The measurements for each of the models were generated and the mean and standard deviation for the each measurement were calculated.

Tables 5, 6, and 7 show the means and standard deviations of linear and angular dentofacial measurements.

Tables 1-8A, referred to herein, are provided in Appendix A to the specification.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

Throughout the description are numbers in [brackets] identifying references which are listed below. Each of the references is incorporated by reference herein, in its entirety.

1. Broadbent B. H. A New X-Ray Technique and Its Application to Orthodontia, *The Angle Orthodontist*: April 1931, Vol. 1, No. 2, pp. 45-66.
2. Hellman, M. The Face and Occlusion of the Teeth, *Man. Int. J. Orthodont.*, 12:921-945, 1927).
3. Steiner C. Cephalometrics for you and me, *Am J Orthod* 1953; 39: 729-55.
4. Jacobson A.: The "Wits" appraisal of jaw disharmony, *Am J Orthod and Dentofacial Orthop* 1975: 67(2); 125-138
5. Moorrees C F, uan Venrooij M E, Lebret L M, Glatky C G, Kent R L, Reed R B. New norms for the mesh diagram analysis. *Am J Orthod.* 1976 January; 69(1):57-71.
6. A Lundstrom, F Lundstrom, L. M. L. Lebret and C. F. A. Moorrees. Natural head position and natural head orientation: basic considerations in cephalometric analysis and research. *Eur J Orthod.* 1995 April; 17(2):111-20.
7. Peck H., Peck S., A Proportional Analysis Of The Soft Tissue Facial Profile In Young Adults With Normal Occlusion. A Concept Of Facial Esthetics., Angle Orthod. 1970; 40(4):284-318.
8. Kohl J V (2006). "*The Mind's Eyes: Human Pheromones, Neuroscience, and Male Sexual Preferences*". *Psychology & Human Sexuality* 18 (4): 313-369.
9. Sforza C, Laino A, D'Alessio R, Grandi G, Binelli M, Ferrario V F (January 2009). "*Soft-tissue facial characteristics of attractive Italian women as compared to normal women*". Angle Orthod 79 (1): 17-23. doi: 10.2319/122707-605.1. PMID 19123721.
10. Cunnigingham has shown that the preference for neonatal features showed the least cross-cultural variability in judging facial attractiveness
11. Cunningham M R, Roberts, A R, Barbee, A P, Druen, P B, Wu, C H (February 1995). "Their ideas of beauty are, on the whole, the same as ours": Consistency and variability in the cross-cultural perception of female physical attractiveness". *Journal of Personality and Social Psychology* 68 (2): 261-279.
12. Cunningham M R (May 1986). "Measuring the Physical in Physical Attractiveness: Quasi-Experiments on the Sociobiology of Female Facial Beauty". *Journal of Personality and Social Psychology* 50 (5): 925-935.
13. Buss, David (2003) [1994]. *The Evolution of Desire* (second ed.). New York: Basic Books. pp. 54, 55. ISBN 0-465-07750-1.
14. Cellerino A. Psychobiology of facial attractiveness. J Endocrinol Invest. 2003; 26(3 Suppl):45-8.
15. Rhodes G, Yoshikawa S, Clark A, Lee K, McKay R, Akamatsu S. Attractiveness of facial averageness and symmetry in non-western cultures: in search of biologically based standards of beauty. Perception. 2001; 30(5): 611-25.
16. Lundström A, Forsberg C M, Peck S, McWilliam J. Angle Orthod. 1992 Summer; 62(2):127-33.
17. Arnett G W, Jelic J S, Kim J, Cummings D R, Beress A, Worley C M Jr, Chung B, Bergman R. Soft tissue cephalometrianalysis:diagnosis and treatment planning of dentofacial deformity. Am J Orthod Dentofacial Orthop. 1999 September; 116(3):239-53.
18. Kochel J, Meyer-Marcotty P, Strnad F, Kochel M, Stellzig-Eisenhauer A. 3D soft tissue analysis—part 1: sagittal parameters. J Orofac Orthop. 2010 January; 71(1): 40-52.
19. Kochel J, Meyer-Marcotty P, Kochel M, Schneck S, Stellzig-Eisenhauer A. 3D soft tissue analysis—part 2: vertical parameters.) Orofac Orthop. 2010 May; 71(3): 207-20.
20. Plooij J M, Swennen G R, Rangel F A, Maal T J, Schutyser F A, Bronkhorst E M, Kuijpers-Jagtman A M, Berge S J. Evaluation of reproducibility and reliability of 3D soft tissue analysis using 3D stereophotogrammetryJnt J Oral Maxillofac Surg. 2009 March; 38(3):267-73.
21. Božič, Kau C H, Richmond S, Ovsenik M, Hren N I. Novel method of 3-dimensional soft-tissue analysis for Class III patients. Am J Orthod Dentofacial Orthop. 2010 December; 138(6):758-69.
22. Whetten J L, Williamson P C, Heo G, Varnhagen C, Major P W. Variations in orthodontic treatment planning decisions of class II patients between virtual 3-dimensional models and traditional plaster study models. Am J Orthod Dentofacial Orthop 2006; 130: 485-491.
23. Fleming P S, Marinho V, Johal A. Orthodontic measurements on digital study models compared with plaster models: a systematic review. Orthod Craniofac Res. 2011; 14: 1-16.
24. Nijkamp P G, Habets L L, Aartman I H, Zentner A. The influence of cephalometrics on orthodontic treatment planning Eur J Orthod, 2008; 30(6):630-5.
25. Turpin D L. British Orthodontic Society revises guidelines for clinical radiography. Am J Orthod Dentofacial Orthop. 2008 November; 134(5):597-8.
26. Isaacson K G, Thom A R, Horner K, Whaites E. Orthodontic radiographs—guidelines for the use of radiographs in clinical orthodontics. 3rd ed. London: British Orthodontic Society; 2008.
27. Making the best use of clinical radiology services: referral guidelines. Royal College of Radiologists. 6th ed. 2007.

28. Ruf S. TMD and the daily orthodontic practice. World J Orthod 2005; 6(Suppl):210.
29. Atchinson K A, Luke L S, White S C. An algorithm for ordering pretreatment orthodontic radiographs. Am J Orthod Dentofacial Orthop 1992; 102:29-44.
30. Smith B R, Park J H, Cederberg R A. An evaluation of cone-beam computed tomography use in postgraduate orthodontic programs in the United States and Canada. J Dent Educ 2011; 75: 98-106.
31. Larson B E. Cone-beam computed tomography is the imaging technique of choice for comprehensive orthodontic assessment. Am J Orthod Dentofacial Orthop. 2012 April; 141(4):402, 404, 406.
32. Pauwels R, Beinsberger J, Collaert B, Theodorakou C, Rogers J, Walker A, et al., The SEDENTEXCT Project Consortium. Effective dose range for dental cone beam computed tomography scanners. Eur J Radiol 2012; 81:267-71.
33. Halazonetis D J. Cone-beam computed tomography is not the imaging choice for comprehensive orthodontic assessment. Am J Orthod Dentofacial Orthop. 2012 April; 141(4):403, 405, 407
34. European Commission. Radiation Protection 136. European guidelines on radiation protection in dental radiology. Luxembourg: Office for Official Publications of the European Communities; 2004: Available at: http://ec.europa.eu/energy/nuclear/radioprotection/publication/doc/136_en.pdf:Accessed on Jan. 20, 2012.
35. American Association of Orthodontists. 2010 AAO member and patient census study. Final report; Jun. 23, 2011.
36. Timock A, Cook V, McDonald T, Leo M C, Crowe J, Benninger B, et al. Accuracy and reliability of buccal bone height and thickness measurements from cone-beam computed tomography imaging. Am J Orthod Dentofacial Orthop 2011; 140:734-44.
37. Leung C C, Palomo L, Griffith R, Hans M G. Accuracy and reliability of cone-beam computed tomography for measuring alveolar bone height and detecting bony dehiscences and fenestrations. Am J Orthod Dentofacial Orthop 2010; 137(4 Suppl):S109-19.
38. Making the best use of clinical radiology services: referral guidelines. Royal College of Radiologists. 6th ed. 2007.
39. Petersson A. What you can and cannot see in TMJ imaging—an overview related to the RDC/TMD diagnostic system. J Oral Rehabil. 2010; 37:771-8.
40. van Vlijmen O J, Kuijpers M A, Bergé S J, Schols J G, Maal T J, Breuning H, Kuijpers-Jagtman A M. Evidence supporting the use of cone-beam computed tomography in orthodontics. J Am Dent Assoc. 2012 March; 143(3):241-52.
41. Pittayapat P, Limchaichana-Bolstad N, Willems G, Jacobs R. Three-dimensional cephalometric analysis in orthodontics: a systematic review. Orthod Craniofac Res. 2013 Dec. 22.
42. Botticelli S, *Verna* C, Cattaneo P M, Heidmann J, Melsen B. Two versus three-dimensional imaging in subjects with unerupted maxillary canines. Eur J Orthod 2011; 33:344-9.
43. Hujoel P, Hollender L, Bollen A M, Young J D, McGee M, Grosso A. Head-and-neck organ doses from an episode of orthodontic care. Am J Orthod Dentofacial Orthop 2008; 133:210-7
44. Rischen R J, Breuning K H, Bronkhorst E M, Kuijpers-Jagtman A M. Records needed for orthodontic diagnosis and treatment planning—a systematic review. PLoS One. 2013 Nov. 12; 8(11):e74186.
45. Huanca Ghislanzoni L T, Lineberger M, Cevidanes L H, Mapelli A, Sforza C, McNamara J A Jr. Evaluation of tip and torque on virtual study models: a validation study. Prog Orthod. 2013 Jul. 26; 14(1):19. doi: 10.1186/2196-1042-14-19.
46. Andrews L. F Straight-wire. The Concept and Appliance, L. A. Wells, San Diego 1989.
47. Farkas L G, Kolar J C, Munro I R. Geography of the nose: a morphometric study. Aesthetic Plast Surg. 1986; 10(4):191-223.
48. Gower, J. C. Generalized procrustes analysis. Psychometrika. 1975; 40: 31-33.
49. Adams, D., Rohlf, F. J., and Slice, D.: Geometric morphometrics: Ten years of progress following the "revolution", Ital. J. Zool., 71, 5-16, 2004.
50. Proffit W R, Jackson T H, Turvey T A. Changes in the pattern of patients receiving surgical-orthodontic treatment. Am J Orthod Dentofacial Orthop. 2013 June; 143 (6):793-8.
51. English W R, Robison S F, Summitt J B, Oesterle L J, Brannon R B, Morlang W M. Individuality of human palatal rugae. J Forensic Sci. 1988; 33:718-26.
52. Dijkstal J M, Bothun E D, Harrison A R, Lee M S. Normal exophthalmometry measurements in a United States pediatric population. Ophthal Plast Reconstr Surg. 2012 January-February; 28(1):54-6.
53. MacLachlan C, Howland H C. Normal values and standard deviations for pupil diameter and interpupillary distance in s ubjectsaged 1 month to 19 years. Ophthalmic Physiol Opt. 2002 May; 22(3): 175-82.
54. Masoud M, Masoud I, Kent R L Jr, Gowharji N, Cohen L E. Assessing skeletal maturity by using blood-spot insulin-like growth factor I (IGF-I) testing. Am J Orthod Dentofacial Orthop 2008; 134(2):209-16.
55. Masoud M I, Masoud I, Kent R L Jr, Gowharji N, Hassan A H, Cohen L E. Relationship between blood-spot insulin-like growth factor 1 levels and hand-wrist assessment of skeletal maturity. Am J Orthod Dentofacial Orthop 2009; 136(1):59-64.
56. Ishaq R A, Soliman S A, Foda M Y, Fayed M M. Insulin-like growth factor I: abiological maturation indicator. Am J Orthod Dentofacial Orthop 2012; 142(5):654-61.
57. Perinetti G, Baccetti T, Contardo L, Di Lenarda R. Gingival crevicular fluid alkaline phosphatase activity as a non-invasive biomarker of skeletal maturation. Orthod Craniofac Res. 2011 February; 14(1):44-50.
58. Masoud M I, Marghalani H Y, Masoud I M, Gowharji N F. Prospective longitudinal evaluation of the relationship between changes in mandibular length and blood-spot IGF-1 measurements. Am J Orthod Dentofacial Orthop 2012; 141(6):694-704.
59. Carlsson R, Ronnerman A. Crown-root angles of upper central incisors. Am J Orthod. 1973 August; 64(2):147-54.
60. Srinivasan B, Kailasam V, Chitharanjan A, Ramalingam A. Relationship between crown-root angulation (collum angle) of maxillary central incisors in Class II, division 2 malocclusion and lower lip line. Orthodontics (Chic.). 2013; 14(1):e66-74.
61. Taylor R M. Variation in form of human teeth: I. An anthropologic and forensic study of maxillary incisors. J Dent Res. 1969 January-February; 48(1):5-16.

62. Ludlow J. B, Walker C., Assessment Of Phantom Dosimetry And Image Quality Of I-Cat Flx Cone-Beam Computed Tomography. Am J Orthod Dentofacial Orthop. 2013 December; 144(6):802-17.

TABLE 1

List of Dental Landmarks and Descriptions

| Table 1 Dental Landmarks | Code | Description |
|---|---|---|
| Peak palatal depth | PD | highest midline point on the palate at the level of the maxillary first molars |
| UR central incisor: FA point | UR1FA | Mid-point of the facial axis of the clinical crown (FACC, defined by the height of contour of the facial surface) |
| UR central incisor: incisal limit of the labial FACC (facial axis of the clinical crown) | UR1I | the point where the incisal edge intersects with the FACC line |
| UR central incisor: Gingival limit of the facial FACC | UR1F | The point where the facial gingival margin intersects with the FACC line |
| UR central incisor: Gingival limit of the palatal FACC | UR1P | The point where the palatal gingival margin intersects with the palatal extension of the FACC line |
| UR central incisor: mesial contact point | UR1M | The height of contour on the mesial surface of the tooth |
| UR central incisor: Distal contact point | UR1D | The height of contour on the distal surface of the tooth |
| UL central incisor: FA point | UL1FA | Mid-point of the facial axis of the clinical crown (defined by the height of contour of the facial surface) |
| UL central incisor: incisal limit of the labial FACC (facial axis of the clinical crown) | UL1I | the point where the incisal edge intersects with the FACC line |
| UL central incisor: Gingival limit of the facial FACC | UL1F | The point where the facial gingival margin intersects with the FACC line |
| UL central incisor: Gingival limit of the palatal FACC | UL1P | The point where the palatal gingival margin intersects with the palatal extension of the FACC line |
| UL central incisor: mesial contact point | UL1M | The height of contour on the mesial surface of the tooth |
| UL central incisor: Distal contact point | UL1D | The height of contour on the distal surface of the tooth |
| UR canine: FA point | UR3FA | Mid-point of the facial axis of the clinical crown (defined by the height of contour of the facial surface) |
| UR canine: canine ridge limit of the labial FACC (facial axis of the clinical crown) | UR3C | the point where the canine ridge intersects with the FACC line |
| UR canine: Gingival limit of the facial FACC | UR3F | The point where the facial gingival margin intersects with the FACC line |
| UR canine: Gingival limit of the palatal FACC | UR3P | The point where the palatal gingival margin intersects with the palatal extension of the FACC line |
| UR canine: mesial contact point | UR3M | The height of contour on the mesial surface of the tooth |
| UR canine: Distal contact point | UR3D | The height of contour on the distal surface of the tooth |
| UL canine: FA point | UL3FA | Mid-point of the facial axis of the clinical crown (defined by the height of contour of the facial surface) |
| UL canine: canine ridge limit of the labial FACC (facial axis of the clinical crown) | UL3C | the point where the canine ridge intersects with the FACC line |
| UL canine: Gingival limit of the facial FACC | UL3F | The point where the facial gingival margin intersects with the FACC line |
| UL canine: Gingival limit of the palatal FACC | UL3P | The point where the palatal gingival margin intersects with the palatal extension of the FACC line |
| UL canine: mesial contact point | UL3M | The height of contour on the mesial surface of the tooth |
| UL canine: Distal contact point | UL3D | The height of contour on the distal surface of the tooth |
| UR first premolar: FA point | UR4FA | Mid-point of the facial axis of the clinical crown (FACC (defined by the height of contour of the facial surface) |
| UR first premolar: occlusal limit of the labial FACC (facial axis of the clinical crown) | UR4O | the point where the occlusal surface intersects with the FACC line |
| UR first premolar: Gingival limit of the facial FACC | UR4F | The point where the facial gingival margin intersects with the FACC line |
| UR first premolar: Gingival limit of the palatal extension of the FACC | UR4P | The point where the palatal gingival margin intersects with the palatal extension of the FACC line |
| UR first premolar mesial contact point | UR4M | The height of contour on the mesial surface of the tooth |

TABLE 1-continued

List of Dental Landmarks and Descriptions

| Table 1 Dental Landmarks | Code | Description |
| --- | --- | --- |
| UR first premolar: Distal contact point | UR4D | The height of contour on the distal surface of the tooth |
| UR first premolar: center of the occlusal surface | UR4C | The point where the line connecting the mesial and distal contact points intersects with the extension of the FACC |
| UL first premolar: FA point | UL4FA | Mid-point of the facial axis of the clinical crown (FACC (defined by the height of contour of the facial surface) |
| UL first premolar: occlusal limit of the labial FACC (facial axis of the clinical crown) | UL4O | the point where the occlusal surface intersects with the FACC line |
| UL first premolar: Gingival limit of the facial FACC | UL4F | The point where the facial gingival margin intersects with the FACC line |
| UL first premolar: Gingival limit of the palatal extension of the FACC | UL4P | The point where the palatal gingival margin intersects with the palatal extension of the FACC line |
| UL first premolar mesial contact point | UL4M | The height of contour on the mesial surface of the tooth |
| UL first premolar: Distal contact point | UL4D | The height of contour on the distal surface of the tooth |
| UL first premolar: center of the occlusal surface | UL4C | The point where the line connecting the mesial and distal contact points intersects with the extension of the FACC |
| UR first molar: FA point | UR6FA | Mid-point of the facial axis of the clinical crown (defined by the dominant buccal groove) |
| UR first molar: occlusal limit of the labial FACC (facial axis of the clinical crown) | UR6O | the point where the occlusal surface intersects with the FACC line |
| UR first molar: Gingival limit of the facial palatal axis | UR6F | The point where the facial gingival margin intersects with the lingual FACC line |
| UR first molar: Gingival limit of the palatal axis | UR6P | The point where the palatal gingival margin intersects with the palatal axis line defined by the palatal groove |
| UR first molar: mesial contact point | UR6M | The height of contour on the mesial surface of the tooth |
| UR first molar: Distal contact point | UR6D | The height of contour on the distal surface of the tooth |
| UR first molar: center of the occlusal surface | UR6C | The point where the line connecting the mesial and distal contact points intersects with the line connecting the faxial and palatal grooves |
| UR first molar: mesiobuccal cusp | UR6MB | tip of the mesiobuccal cusp of the tooth |
| UR first first molar: Mesiopalatal cusp | UR6MP | tip of the mesiopalatal cusp of the tooth |
| UL first molar: FA point | UL6FA | Mid-point of the facial axis of the clinical crown (defined by the dominant buccal groove) |
| UL first molar: occlusal limit of the labial FACC (facial axis of the clinical crown) | UL6O | the point where the occlusal surface intersects with the FACC line |
| UL first molar: Gingival limit of the facial FACC | UL6F | The point where the facial gingival margin intersects with the lingual FACC line |
| UL first molar: Gingival limit of the palatal axis | UL6P | The point where the palatal gingival margin intersects with the palatal axis line defined by the palatal groove |
| UL first molar: mesial contact point | UL6M | The height of contour on the mesial surface of the tooth |
| UL first molar: Distal contact point | UL6D | The height of contour on the distal surface of the tooth |
| UL first molar: center of the occlusal surface | UL6C | The point where the line connecting the mesial and distal contact points intersects with the line connecting the faxial and palatal grooves |
| UL first molar: mesiobuccal cusp | UL6MB | tip of the mesiobuccal cusp of the tooth |
| UL first molar: mesiopalatal cusp | UL6MP | tip of the mesiopalatal cusp of the tooth |
| LR central incisor: FA point | LR1FA | Mid-point of the facial axis of the clinical crown (defined by the height of contour of the facial surface) |
| LR central incisor: incisal limit of the labial FACC (facial axis of the clinical crown) | LR1I | the point where the incisal edge intersects with the FACC line |
| LR central incisor: Gingival limit of the facial FACC | LR1F | The point where the facial gingival margin intersects with the FACC line |
| LR central incisor: Gingival limit of the lingual FACC | LR1L | The point where the lingual gingival margin intersects with the palatal extension of the FACC line |

TABLE 1-continued

List of Dental Landmarks and Descriptions

| Table 1 Dental Landmarks | Code | Description |
| --- | --- | --- |
| LR central incisor: mesial contact point | LR1M | The height of contour on the mesial surface of the tooth |
| LR central incisor: Distal contact point | LR1D | The height of contour on the distal surface of the tooth |
| LL central incisor: FA point | LL1FA | Mid-point of the facial axis of the clinical crown (defined by the height of contour of the facial surface) |
| LL central incisor: incisal limit of the labial FACC (facial axis of the clinical crown) | LL1I | the point where the incisal edge intersects with the FACC line |
| LL central incisor: Gingival limit of the facial FACC | LL1F | The point where the facial gingival margin intersects with the FACC line |
| LL central incisor: Gingival limit of the lingual FACC | LL1L | The point where the lingual gingival margin intersects with the palatal extension of the FACC line |
| LL central incisor: mesial contact point | LL1M | The height of contour on the mesial surface of the tooth |
| LL central incisor: Distal contact point | LL1D | The height of contour on the distal surface of the tooth |
| LR canine: FA point | LR3FA | Mid-point of the facial axis of the clinical crown (defined by the height of contour of the facial surface) |
| LR canine: canine ridge limit of the labial FACC (facial axis of the clinical crown) | LR3C | the point where the canine ridge intersects with the FACC line |
| LR canine: Gingival limit of the facial FACC | LR3F | The point where the facial gingival margin intersects with the FACC line |
| LR canine: Gingival limit of the lingual FACC | LR3L | The point where the palatal gingival margin intersects with the Lingual extension of the FACC line |
| LR caniner: mesial contact point | LR3M | The height of contour on the mesial surface of the tooth |
| LR canine: Distal contact point | LR3D | The height of contour on the distal surface of the tooth |
| LL canine: FA point | LL3FA | Mid-point of the facial axis of the clinical crown (defined by the height of contour of the facial surface) |
| LL canine: canine ridge limit of the labial FACC (facial axis of the clinical crown) | LL3C | the point where the canine ridge intersects with the FACC line |
| LL canine: Gingival limit of the facial FACC | LL3F | The point where the facial gingival margin intersects with the FACC line |
| LL canine: Gingival limit of the lingual FACC | LL3L | The point where the palatal gingival margin intersects with the Lingual extension of the FACC line |
| LL canine: mesial contact point | LL3M | The height of contour on the mesial surface of the tooth |
| LL canine: Distal contact point | LL3D | The height of contour on the distal surface of the tooth |
| LR first premolar: FA point | LR4FA | Mid-point of the facial axis of the clinical crown (FACC, defined by the height of contour of the facial surface) |
| LR first premolar: occlusal limit of the labial FACC (facial axis of the clinical crown) | LR4O | the point where the occlusal surface intersects with the FACC line |
| LR first premolar: Gingival limit of the facial FACC | LR4F | The point where the facial gingival margin intersects with the FACC line |
| LR first premolar: Gingival limit of the lingual extension of the FACC | LR4L | The point where the lingual gingival margin intersects with the lingual extension of the FACC line |
| LR first premolar mesial contact point | LR4M | The height of contour on the mesial surface of the tooth |
| LR first premolar: Distal contact point | LR4D | The height of contour on the distal surface of the tooth |
| LR first premolar: center of the occlusal surface | LR4C | The point where the line connecting the mesial and distal contact points intersects with the extension of the FACC |
| LL first premolar: FA point | LL4FA | Mid-point of the facial axis of the clinical crown (FACC, defined by the height of contour of the facial surface) |
| LL first premolar: occlusal limit of the labial FACC (facial axis of the clinical crown) | LL4O | the point where the occlusal surface intersects with the FACC line |
| LL first premolar: Gingival limit of the facial FACC | LL4F | The point where the facial gingival margin intersects with the FACC line |
| LL first premolar: Gingival limit of the facial FACC | LL4L | The point where the lingual gingival margin intersects with the lingual extension of the FACC line |

TABLE 1-continued

List of Dental Landmarks and Descriptions

| Table 1 Dental Landmarks | Code | Description |
| --- | --- | --- |
| LL first premolar mesial contact point | LL4M | The height of contour on the mesial surface of the tooth |
| LL first premolar: Distal contact point | LL4D | The height of contour on the distal surface of the tooth |
| LL first premolar: center of the occlusal surface | LL4C | The point where the line connecting the mesial and distal contact points intersects with the extension of the FACC |
| LR first molar: FA point | LR6FA | Mid-point of the facial axis of the clinical crown (defined by the dominant buccal groove) |
| LR first molar: occlusal limit of the labial FACC (facial axis of the clinical crown) | LR6O | the point where the occlusal surface intersects with the FACC line |
| LR first molar: Gingival limit of the facial FACC | LR6F | The point where the facial gingival margin intersects with the lingual FACC line |
| LR first molar: Gingival limit of the lingual axis | LR6L | The point where the lingual gingival margin intersects with the lingual axis line defined by the lingual groove |
| LR first molar: mesial contact point | LR6M | The height of contour on the mesial surface of the tooth |
| LR first molar: Distal contact point | LR6D | The height of contour on the distal surface of the tooth |
| LR first molar: center of the occlusal surface | LR6C | The point where the line connecting the mesial and distal contact points intersects with the line connecting the facial and lingual grooves |
| LR first molar: mesiobuccal cusp | LR6MB | tip of the mesiobuccal cusp of the tooth |
| LL first molar: FA point | LL6FA | Mid-point of the facial axis of the clinical crown (defined by the dominant buccal groove) |
| LL first molar: occlusal limit of the labial FACC (facial axis of the clinical crown) | LL6O | the point where the occlusal surface intersects with the FACC line |
| LL first molar: Gingival limit of the facial FACC | LL4F | The point where the facial gingival margin intersects with the lingual FACC line |
| LL first molar: Gingival limit of the lingual axis | LL6L | The point where the lingual gingival margin intersects with the lingual axis line defined by the lingual groove |
| LL first molar: mesial contact point | LL6M | The height of contour on the mesial surface of the tooth |
| LL first molar: Distal contact point | LL6D | The height of contour on the distal surface of the tooth |
| LL first molar: center of the occlusal surface | LL6C | The point where the line connecting the mesial and distal contact points intersects with the line connecting the facial and lingual grooves |
| LL first molar: mesiobuccal cusp | LL6MB | tip of the mesiobuccal cusp of the tooth |

TABLE 2

Dental Lines (Axes) and Descriptions

| Dental Lines | Code | Description |
| --- | --- | --- |
| Upper right central incisor: Long axis | UR1LA | A line connecting UR1I and the midpoint between UR1F and UR1P |
| Upper right central incisor: FACC | UR1FACC | Facial axis of the clinical crown defined by the height of contour of the facial surface |
| Upper right central incisor: tangent to FA point | UR1FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Upper left central incisor: Long axis | UL1LA | A line connecting UL1I and the midpoint between UL1F and UL1P |

TABLE 2-continued

Dental Lines (Axes) and Descriptions

| Dental Lines | Code | Description |
| --- | --- | --- |
| Upper left central incisor: FACC | UL1FACC | Facial axis of the clinical crown defined by the height of contour of the facial surface |
| Upper left central incisor: tangent to FA point | UL1FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Upper right canine: Long axis | UR3LA | A line connecting UR3C and the midpoint between UR3F and UR3P |
| Upper right canine: FACC | UR3FACC | Facial axis of the clinical crown defined by the height of contour of the facial surface |
| Upper right canine: tangent to FA point | UR3FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Upper left canine: Long axis | UL3LA | A line connecting UL3C and the midpoint between UL3F and UL3P |
| Upper left canine: FACC | UL3FACC | Facial axis of the clinical crown defined by the height of contour of the facial surface |
| Upper left canine: tangent to FA point | UL3FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Upper right first premolar: Long axis | UR4LA | A line connecting UR4C and the midpoint between UR4F and UR4P |
| Upper right first premolar: FACC | UR4FACC | Facial axis of the clinical crown defined by the height of contour of the facial surface |
| Upper right first premolar: tangent to FA point | UR4FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Upper left first premolar: Long axis | UL4LA | A line connecting UL4C and the midpoint between UL4F and UL4P |
| Upper left first premolar: FACC | UL4FACC | Facial axis of the clinical crown defined by the height of contour of the facial surface |
| Upper left first premolar: tangent to FA point | UL4FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Upper right first molar: Long axis | UR6LA | A line connecting UR6C and the midpoint between UR6F and UR6P |

TABLE 2-continued

Dental Lines (Axes) and Descriptions

| Dental Lines | Code | Description |
| --- | --- | --- |
| Upper right first molar: FACC | UR6FACC | Facial axis of the clinical crown defined by the height of contour of the facial surface |
| Upper right first molar: tangent to FA point | UR6FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Upper left first molar: Long axis | UL6LA | A line connecting UL6C and the midpoint between UL6F and UL6P |
| Upper left first molar: FACC | UL6FACC | Facial axis of the clinical crown defined by the height of contour of the facial surface |
| Upper left first molar: tangent to FA point | UL6FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower right central incisor: Long axis | LR1LA | A line connecting LR1I and the midpoint between LR1F and LR1L |
| Lower right central incisor: FACC | LR1FACC | Facial axis of the clinical crown defined by the height of contour of the facial surface |
| Lower right central incisor: tangent to FA point | LR1FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower left central incisor: Long axis | LL1LA | A line connecting LL1I and the midpoint between UL1F and UL1L |
| Lower left central incisor: FACC | LL1FACC | Facial axis of the clinical crown defined by the height of contour of the facial surface |
| Lower left central incisor: tangent to FA point | LL1FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower right canine: Long axis | LR3LA | A line connecting LR3C and the midpoint between LR3F and LR3L |
| Lower right canine: FACC | LR3FACC | Facial axis of the clinical crown defined by the height of contour of the facial surface |
| Lower right canine: tangent to FA point | LR3FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower left canine: Long axis | LL3LA | A line connecting LL3C and the midpoint between LL3F and LL3L |

TABLE 2-continued

Dental Lines (Axes) and Descriptions

| Dental Lines | Code | Description |
| --- | --- | --- |
| Lower left canine: FACC | LL3FACC | Facial axis of the clinical crown defined by the height of contour of the facial surface |
| Lower left canine: tangent to FA point | LL3FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower right first premolar: Long axis | LR4LA | A line connecting LR4C and the midpoint between LR4F and LR4L |
| Lower right first premolar: FACC | LR4FACC | Facial axis of the clinical crown defined by the height of contour of the facial surface |
| Lower right first premolar: tangent to FA point | LR4FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower left first premolar: Long axis | LL4LA | A line connecting LL4C and the midpoint between LL4F and LL4L |
| Lower left first premolar: FACC | LL4FACC | Facial axis of the clinical crown defined by the height of contour of the facial surface |
| Lower left first premolar: tangent to FA point | LL4FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower right first molar: Long axis | LR6LA | A line connecting LR6C and the midpoint between LR6F and LR6L |
| Lower right first molar: FACC | LR6FACC | Facial axis of the clinical crown defined by the height of contour of the facial surface |
| Lower right first molar: tangent to FA point | LR6FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |
| Lower left first molar: Long axis | LL6LA | A line connecting LL6C and the midpoint between LL6F and LL6L |
| Lower left first molar: FACC | LL6FACC | Facial axis of the clinical crown defined by the height of contour of the facial surface |
| Lower left first molar: tangent to FA point | LL6FAT | A line tangent to the FA point (can be constructed by drawing a line from the FA point to the occlusal extension of the FACC and another line from the FA point to the gingival extension of the FACC. A perpendicular from the middle of each of those lines can then be drawn. The tangent to the FA point would be perpendicular to a line connecting the intersection of those two lines to the FA point |

TABLE 3

Facial Landmarks and Descriptions.

| Facial Landmarks | Code | Description |
|---|---|---|
| Lips at Rest Landmarks | | |
| trichion | tr | The point located at hairline in the midline of the forehead |
| Glabella | g | The most anterior midpoint on the fronto-orbital soft tissue contour |
| Orbitale superius (left) | os l | The most superior soft tissue point of the lower border of left eyebrow |
| Orbitale superius (right) | os r | The most superior soft tissue point of the lower border of right eyebrow |
| endocanthion (left) | en l | The soft tissue point located at the inner commissure of left eye fissure |
| endocanthion (right) | en r | The soft tissue point located at the inner commissure of right eye fissure |
| exocanthion (left) | ex l | The soft tissue point located at the outer commissure of left eye fissure |
| exocanthion (right) | ex | The soft tissue point located at the outer commissure of right eye fissure |
| pupil point (left) | Pu l | Middle of the left pupil |
| Pupil point (right) | Pu r | Middle of the right pupil |
| pupil reconstructed point | M | The point located midway between the pupils (this represents the 0,0,0 point) |
| Nasion | n | The most posterior point of the frontonasal soft tissue contour in the midline of the base of the nasal root, The deepest point on the nasal bridge |
| orbitale (left) | or | The soft tissue point located at one distance of the normal opened eye down from left lower eyelid. |
| orbitale (right) | or | The soft tissue point located at one distance of the normal opened eye down from right lower eyelid. |
| soft tissue zygion (left) | st zy l | The soft tissue point located at left intersection of the lines orbitale-soft tissue porion and exocanthion-subaurale |
| soft tissue zygion (right) | st zy r | The soft tissue point located at right intersection of the lines orbitale-soft tissue porion and exocanthion-subaurale |
| Malar eminence (left) | ma l | The most prominent point on the cheek area beneath the outer canthus and slightly medial to the vertical line passing through it |
| Malar eminence (right) | ma r | The most prominent point on the cheek area beneath the outer canthus and slightly medial to the vertical line passing through it |
| tragion (left) | t l | The point located at the most concave point of the insertion of the upper margin of left tragus |
| tragion (right) | t r | The point located at the most concave point of the insertion of the upper margin of right tragus |
| soft tissue porion (left) | st po l | The point located at each insertion of the crus helices in the cavitas conchalis |
| soft tissue porion (right) | st po r | The point located at each insertion of the crus helices in the cavitas conchalis |
| subaurale (left) | sba l | The lowest point on the free margin of each ear lobe |
| subaurale (right) | sba r | The lowest point on the free margin of each ear lobe |
| pronasale | pm | The most anterior midpoint of nasal tip |
| columella constructed point | cc | the midpoint of the columella creast at the level of the nostril top points |
| alar curvature (left) | ac l | The point located at the facial insertion of the left alar base |
| alar curvature (right) | ac r | The point located at the facial insertion of the right alar base |
| alare(left) | al l | the most lateral point on left alar contour |
| alare(right) | al r | the most lateral point on right alar contour |
| nostril anterior (left) | na l | The most anterior point of the left nostril |
| nostril anterior (right) | na r | The most anterior point of the right nostril |
| nostril base (left) | nb l | The lowest point of the left nostril from the submental view or the most posterior point on the nostril in the sagittal view |
| nostril base (right) | nb r | The lowest point of the right nostril from the submental view or the most posterior point on the nostril in the sagittal view |
| subnasale | sn | the midpoint on the nasolabial soft tissue contour between the columella crest and the upper lip |
| subspinale (soft tissue A) | SA | The most posterior midpoint of the philtrum (deepest midline point between the subnasale and labiale superius). Also soft tissue point A. |

TABLE 3-continued

Facial Landmarks and Descriptions.

| Facial Landmarks | Code | Description |
| --- | --- | --- |
| Christa philtri (left) | cph l | The point at left crossing of the vermilion line and the elevated margin of the philtrum |
| Christa philtri (right) | cph r | The point at right crossing of the vermilion line and the elevated margin of the philtrum |
| Chelion(left) | ch l | The point located at the left labial commissure |
| Chelion(right) | ch r | The point located at the right labial commissure |
| labiale superius | ls | The midpoint of the vermilion line of the upper lip. |
| inferior stomion | sti | the midpoint of the upper border of the lower lip |
| upper stomion | stu | The midpoint of the lower border of the upper lip |
| labiale inferius | li | The midline of the vermilion line of the lower lip |
| soft tissue gonion (left) | st go l | The most lateral point on the soft tissue contour of left mandibular angle located at the intersection of the tangent lines of the posterior border and the inferior border of the margin of the lower face |
| soft tissue gonion (right) | st go r | The most lateral point on the soft tissue contour of right mandibular angle located at the intersection of the tangent lines of the posterior border and the inferior border of the margin of the lower face |
| sublabiale (soft tissue B point) | SB | The most posterior midpoint on the labiomental soft tissue contour that defines soft tissue contour that defines the border between the lower lip and the chin. Also soft tissue point B |
| soft tissue pogonion | st pg | The most anterior midpoint of the chin |
| soft tissue gnathion | st gn | The most anterior inferior midpoint of the soft tissue contour of the chin. |
| Menton | st me | Lowest median landmark on the lower border of the mandible |
| Smiling View Landmarks | | |
| inferior stomion (smile) | st(i) s | the midpoint of the upper border of the lower lip on smiling |
| upper stomion (smile) | st(u) s | The midpoint of the lower border of the upper lip on smiling |
| labiale superius (smile) | ls s | The midpoint of the vermilion line of the upper lip on smiling |
| labiale inferius (smile) | li s | The midline of the vermilion line of the lower lip on smiling |
| Chelion(left) (smile) | ch l s | The point located at the left labial commissure on smiling |
| Chelion(right) (smile) | ch r s | The point located at the right labial commissure on smiling |
| inferior stomion (smile) | st(i) s | the midpoint of the upper border of the lower lip on smiling |
| upper stomion (smile) | st(u) s | The midpoint of the lower border of the upper lip on smiling |
| sublabiale (smile) | SA s | The most posterior midpoint on the labiomental soft tissue contour that defines soft tissue contour that defines the border between the lower lip and the chin on smiling |
| subspinale (smile) | SB s | The most posterior midpoint of the philtrum on smiling |

TABLE 4

Description of the Planes.

| Planes | Description |
| --- | --- |
| MA plane | An axial plane passing through the pupils parallel to the true Horizontal determined by the patient's NHP |
| MC plane | A coronal plane passing through the centers of the pupils perpendicular to the true Horizontal determined by the patient's NHP |
| rtMS plane | Sagittal plane going through the right pupil perpendicular to the true Horizontal determined by the patient's NHP |
| ltMS plane | Sagittal plane going through the left pupil perpendicular to the true Horizontal determined by the patient's NHP |
| MS plane | Mid-Sagittal plane going through the M point (midpoint between the pupils) perpendicular to the true Horizontal determined by the patient's NHP |
| ACP plane (alar curvature pupillary plane) | A plane connecting M, ac r, and ac l |
| SNP plane (Subnasale pupillary plane) | A plane connecting Pur, Pul, and Sn |
| SAP plane (Soft tissue A pupillary plan) | A plane connecting SA point, Pur, and Pul |
| LSP plane (Lubrale superius pupillary plane) | A plane connecting Ls, Pur, and Pul |

TABLE 4-continued

Description of the Planes.

| Planes | Description |
|---|---|
| LIP (Lubrale inferius pupillary plane) | A plane connecting the Li, Pur, and Pul |
| SBP (sub labiale puplillary plane) | A plane connecting SB point, Pur, and Pul |
| SPgP (Pogonion pupillary plane) | A plane connecting St Pg, Pur, and Pul |
| MxO plane (maxillary occlusal plane) | Plane connecting UR6MB,UL6MB, and midway between UL4O and UR4O (best fit) |
| MdO plane (Mandibular occlusal plane) | Plane connecting LR6MB, LL6MB, and midway between LL4O and LR4O |
| FO plane (functional occlusal plane) | average of the MxO and MdO |
| MP (Mandibular plane) | A plane connecting st go l, st go r, and st gn |

TABLE 5

Measurements.

| Measurement | MEAN | STDEV |
|---|---|---|
| Sagittal position of the maxilla and maxillary teeth | | |
| Distance Ma (r)-MC plane | 0.646917641 | 1.996719925 |
| Distance Ma (l)-MC plane | −0.943287872 | 2.212201588 |
| Distance ac (r)-MC plane | 11.92512905 | 3.409204847 |
| Distance ac (l)-MC plane | 11.63212319 | 3.879806729 |
| ACP-MCP angle | 175.3312241 | 2.544868766 |
| Distance sn-MC plane | 21.64955534 | 3.971141958 |
| SNP-MCP angle | 25.89913526 | 4.559683719 |
| Distance SA-MC plane | 19.26869225 | 3.564914617 |
| SAP-MCP angle | 20.70666921 | 3.677466478 |
| Distance ls-MC plane | 21.59439022 | 3.532727111 |
| LSP-MCP angle | 20.33998777 | 3.012978028 |
| Distance UR1I-MC plane | 10.46614858 | 3.668053086 |
| UR1LA-MCP angle | 95.8135702 | 3.383366875 |
| Distance ul1i-MC plane | 10.09532165 | 4.32845976 |
| UL1LA-MCP angle | 95.79273444 | 3.437017408 |
| Vertical position of the maxilla and maxillary teeth | | |
| Distance acr-MA plane | −43.02089386 | 2.431721599 |
| Distance aca-MA plane | −42.97439789 | 2.545619954 |
| Distance sn-MA plane | −44.25460268 | 2.524298157 |
| Distance stu-MA plane | −63.57771487 | 3.593871548 |
| Distance stu-sn | 19.71944352 | 2.237981008 |
| MxO-MAP angle | 74.29580688 | 3.146624089 |
| Distance pd-MxO plane | 6.901442519 | 2.438796465 |
| Distance ur3c-MA plane | −66.01867082 | 2.790872728 |
| Distance ul3c-MA plane | −65.76003109 | 2.459868604 |
| Distance ur6mb-MA plane | −63.05150049 | 3.067456295 |
| Distance ul6mb-MA plane | −62.46499425 | 3.198004185 |
| Distance ur1i-MA plane | −67.18940049 | 2.783126759 |
| Distance ul1i-MA plane | −67.10526726 | 2.234266029 |
| Distance ur1i-stu | 9.561877289 | 1.874877762 |
| Distance ul1i-stu | 9.694650747 | 1.819219336 |
| Transverse position of the maxilla and maxillary teeth | | |
| Distance stzyr-rtMs plane | −35.06534972 | 1.663751993 |
| Distance stzyl-ltMs plane | 32.91014776 | 1.802187302 |
| Distance alr-MS plane | −16.29665308 | 2.037701257 |
| Distance all-MS plane | 15.33461164 | 1.314850638 |
| Distance chr-MS plane | −23.45793108 | 6.271439575 |
| Distance chl-MS plane | 22.06994035 | 6.22332895 |
| Distance stzyr-stzyl | 128.7334298 | 4.591548316 |
| Distance alr-all | 31.70924664 | 2.625283921 |
| Distance ur3p-MS plane | −12.63272572 | 1.623069337 |
| Distance ul3p-MS plane | 11.37817997 | 1.35040849 |

TABLE 5-continued

Measurements.

| Measurement | MEAN | STDEV |
|---|---|---|
| Distance ur3p-ul3p | 24.06655531 | 1.756327168 |
| Distance ur6p-MS plane | −18.61971959 | 1.949641079 |
| Distance ul6p-MS plane | 16.66440721 | 1.700223395 |
| Distance ur6p-ul6p | 31.69375901 | 14.98995988 |
| Distance ur3f-MS plane | −18.53693574 | 1.530154662 |
| Distance ul3f-MS plane | 17.34221423 | 1.053057337 |
| Distance ur6f-MS plane | −28.63169454 | 1.911361201 |
| Distance ul6f-MS plane | 26.93044633 | 1.69215061 |
| Distance ur3c-MS plane | −17.71391322 | 1.527012428 |
| Distance ul3c-MS plane | 16.4631959 | 1.353044205 |
| Distance ur3c-ul3c | 34.23279959 | 1.639379691 |
| Distance ur6mp-MS plane | −21.1508721 | 1.820483501 |
| Distance ul6mp-MS plane | 19.33140085 | 1.841389579 |
| Distance ur6mp-ul6mp | 40.54963515 | 2.251475104 |
| MxO-MSP angle | 90.98883159 | 2.767312814 |
| UR3LA-MSP angle | 78.1947786 | 1.279583174 |
| UL3LA-MSP angle | 101.8602243 | 1.368527928 |
| UR6LA-MSP angle | 74.46732238 | 1.23652412 |
| UL6LA-MSP angle | 105.2125328 | 2.194129777 |

TABLE 6

Measurements.

| Measurement | MEAN | STDEV |
|---|---|---|
| Sagittal Position Of The Mandible And Mandibular Teeth | | |
| Distance SB-MC plane | 13.07260433 | 3.508756591 |
| SBP-MC angle | 9.375443577 | 2.552860396 |
| Distance li-MC plane | 18.49752611 | 4.111088656 |
| Distance pg-MC plane | 13.54066154 | 3.786755155 |
| SPgP-MC angle | 8.487900122 | 2.40165274 |
| Distance lr1i-MC plane | 8.030459938 | 3.631567217 |
| Distance ll1i-MC plane | 7.56083929 | 4.148663935 |
| LR1LA-MCP angle | 126.1031774 | 7.251465669 |
| LL1LA-MCP angle | 125.2740682 | 7.4772397 |
| LR1LA-MPP angle | 157.7522204 | 25.01310385 |
| LL1LA-MPP angle | 157.3217418 | 25.47312542 |
| Sagittal Position Of The Mandible And Mandibular Teeth | | |
| Distance SB-MA plane | −80.15506156 | 3.667738471 |
| Distance stpg-MA plane | −92.59979286 | 4.700723534 |
| Distance stme-MA plane | −106.1534366 | 4.757548641 |
| Distance stgor-MA plane | −75.13457253 | 5.997883436 |
| Distance stgol-MA plane | −72.38371968 | 6.797467608 |
| Distance stme-sti | 43.84005521 | 7.237841649 |
| MP-MAr angle | 19.915944 | 3.518877711 |
| tr-stgor-stgn angle | 128.5690666 | 3.346823079 |
| tr-stgor-stgn angle | 129.7171639 | 3.819415203 |
| Distance lr1i-MA plane | −65.09413269 | 2.962140327 |
| Distance ll1i-MA plane | −64.85825679 | 2.778203546 |
| Distance lr1i-MP plane | 32.45975677 | 2.824388773 |
| Distance ll1i-MP plane | 32.4434389 | 2.839666374 |
| Distance lr3c-MP plane | 31.8370152 | 2.65908196 |
| Distance ll3c-MP plane | 31.28743997 | 2.755667187 |
| Distance lr6mb-MP plane | 27.29588227 | 3.525364668 |
| Distance ll6mb-MP plane | 26.84358955 | 4.039564945 |
| FO-MP angle | 167.8754737 | 5.186716173 |
| Transverse Position Of The Mandible And Mandibular Teeth | | |
| Distance stgor-MS plane | −54.3621548 | 3.399694728 |
| Distance stgol-MS plane | 52.96528881 | 3.631091628 |
| Distance stgol-stgor | 107.5033989 | 3.94734262 |
| Distance lr3f-MS plane | −14.57147061 | 1.364809225 |
| Distance ll3f-MS plane | 13.64323587 | 1.394639984 |
| Distance lr6f-MS plane | −26.77717417 | 1.86538517 |
| Distance ll6f-MS plane | 24.99596384 | 1.485932918 |
| Distance ll3f-lr3f | 28.28830705 | 1.545670825 |
| Distance ll6f-lr6f | 51.87781001 | 1.911033805 |

TABLE 6-continued

Measurements

| Measurement | MEAN | STDEV |
|---|---|---|
| Distance lr3c-MS plane | −13.56878956 | 1.099443625 |
| Distance ll3c-MS plane | 12.58410309 | 1.209361362 |
| Distance ll3c-lr3c | 26.22781782 | 1.055423574 |
| Distance lr6c-MS plane | −19.32249159 | 9.65931579 |
| Distance ll6c-MS plane | 17.41753353 | 9.816238923 |
| Distance ll6c-lr6c | 41.28610104 | 1.846164397 |
| lR3LA-MSP angle | 79.48440549 | 5.308551389 |
| UL3LA-MSP angle | 99.06776952 | 7.736230729 |
| UR6LA-MSP angle | 100.8165522 | 21.10776612 |
| LR6LA-MSP angle | 77.12121285 | 18.39233866 |
| Sagittal Intermaxillary Relationships | | |
| Distance SA-MCP-SB-MCP | 6.196087915 | 1.542307933 |
| SAP-SBP angle | 11.47557354 | 1.713184289 |
| Distance SN-MCR- STPG-MCR | 8.108893802 | 2.247245859 |
| SNP-SPGP angle | 17.60101108 | 2.724924964 |
| Distance PG-MCP-ALR-MCP | 3.857739959 | 2.707286797 |
| Distance ur1i-lr1i | 3.99986197 | 1.071889613 |
| Distance ul1i-ll1i | 4.148409674 | 1.248250353 |
| Distance ur3c-lr3d | 3.80412593 | 1.44307756 |
| Distance ul3c-ll3d | 3.690070977 | 0.791440272 |
| Distance ur6mb-lr6o | 3.041544381 | 0.920398749 |
| Distance ul6mb-ll6o | 3.178221643 | 1.218761917 |
| Transverse Intermaxillary Relationships | | |
| Distance stzy-stgo | 21.23003092 | 3.674347089 |
| Distance ur3f-ul3f -lr3f-ll3f | 7.656804295 | 1.590117769 |
| Distance ur6f-ul6f-lr6f-ll6f | 3.762303761 | 1.257012071 |
| Distance ur3c-ul3c-lr3c-ll3c | 8.00498177 | 1.032582224 |
| Distance ur6f-ul6f-lr6f-ll6f | −0.736465897 | 1.228276783 |
| Vertical Intermaxillary Relationships | | |
| Distance sn-stme | 65.33588219 | 6.100437523 |
| Ratio sn-stu/sn-stme | 0.303132942 | 0.035224461 |
| Distance tr-stgor | 61.03605269 | 5.539231108 |
| Distance tl-stgol | 57.71260081 | 5.202545587 |

TABLE 7

Measurements

| Measurement | MEAN | STDEV |
|---|---|---|
| Smile Measurements | | |
| Upper right incisal display | 10.71019188 | 1.482535485 |
| Upper left incisal display | 10.75165415 | 1.39222408 |
| Upper right gingival display | 5.274276839 | 1.018802488 |
| Upper left gingival display | 5.528043203 | 0.902604228 |
| Smile width | 63.21560498 | 3.178043274 |

TABLE 8

Analysis Measurements

| | EXPLANATION OF MEASUREMENTS |
|---|---|
| SKELETAL MEASUREMENTS | |
| MAXILLA | |
| A/P | |
| Maxillary Sagittal Position | A/P position of Maxilla at Alar Base |
| Maxillary Apical Base Position (mm) | A/P position of Maxilla at ST A Point (Affected by incisor position) |
| Maxillary Lip Position (mm) | A/P position of Labial Superius |
| Vertical | |
| Maxillary Vertical Position (mm) | Vertical position of Maxilla at Alar Base |
| MANDIBLE | |
| A/P | |
| Mandibular Apical Base Position(mm) | A/P position of Mandible at ST B Point (affected by incisor position) |
| Mandibular Lip Position (mm) | A/P position of Labiale Inferius |
| Chin Position (mm) | A/P position of ST Pogonion |
| Vertical | |
| Total Anterior Face Height (mm) | Distance from ST Menton to Axial Plane |
| Posterior Face Height (mm) | Distance from ST Gonion to Axial Plane |
| Mandibular Plane Angle (°) | Angle between Mandibular Plane and Coronal Plane |
| INTERMAXILLARY | |
| A/P | |
| Intermaxillary Angle (°) | Angle between Alar Base and ST Pogonion |
| Intermaxillary Apical Base Angle (°) | Angle between ST A point and ST B point |
| Maxillo-Mandibular Differential (mm) | Horizontal distance between Alar Base and ST Pogonion |
| Occlusal Plane Angle (°) | Angle between Functional Occlusal Plane and Coronal plane |
| Vertical | |
| Lower Face Height (mm) | Distance from Subnasale to ST Menton |
| Transverse | |
| Maxillary Cant Angle (°) | Angle between Maxillary Transverse Occlusal plane and Sagittal Plane |
| DENTAL MEASUREMENTS | |
| MAXILLA | |
| A/P | |
| Maxillary Incisors (mm) | A/P position of Maxillary Incisors |
| Maxillary Incisors (°) | A/P angulation of Maxillary Incisors |
| Vertical | |
| Anterior Alveolar Height (mm) | Vertical distance between top of Maxilla and Maxillary Incisors |
| Posterior Alveolar Height (mm) | Vertical distance between top of Maxilla and Maxillary 1st Molars |
| MANDIBLE | |
| A/P | |
| Mandibular Incisors (mm) | A/P position of Mandibular Incisors |
| Mandibular Incisors (°) | A/P angulation of Mandibular Incisors |

TABLE 8A

| | | | | | Number of Deviations | | |
|---|---|---|---|---|---|---|---|
| | Explanation | Value | Norm | SD | from norm | | comments |
| SKELETAL MEASUREMENTS | | | | | | | |
| MAXILLA | | | | | | | |
| A/P | | | | | | | |
| Maxillary Sagittal Position | Perpendicular distance from the alar base to the MC-plane | 16.4 | 11.8 | 3.6 | 1.3 | * | <2 σ |
| Maxillary Apical Base Position(mm) | Perpendicular distance from soft tissue A point to the MC-plane | 28.1 | 19.3 | 3.6 | 2.5 | ** | <3 σ |
| Maxillary Lip Position(mm) | Perpendicular distance from lubrale superius to the MC-plane | 34.6 | 21.6 | 3.5 | 3.7 | *** | >3 σ |
| Vertical | | | | | | | |
| Maxillary Vertical Position (mm) | Perpendicular distance from the alar base to the MA-plane | 44.2 | 43.0 | 2.5 | 0.5 | | |
| MANDIBLE | | | | | | | |
| A/P | | | | | | | |
| Mandibular Apical Base Position (mm) | Perpendicular distance from soft tissue B point to the MC-plane | 18.9 | 13.1 | 3.5 | 1.6 | * | <2 σ |
| Mandibular Lip Position (mm) | Perpendicular distance from lubrale inferius to the MC-plane | 28.5 | 18.5 | 4.1 | 2.4 | ** | <3 σ |
| Chin Position (mm) | Perpendicular distance from soft tissue pogonion to the MC-plane | 18.2 | 13.5 | 3.8 | 1.2 | * | <2 σ |
| Vertical | | | | | | | |
| Total Anterior Face Height(mm) | Perpendicular distance from soft tissue menton to MA-plane | 114.8 | 106.2 | 4.8 | 1.8 | * | <2 σ |
| Posterior Face Height(mm) | Perpendicular distance in from soft tissue gonion to the MA-plane (right and left average) | 83.0 | 73.75913064 | 6.474732239 | 1.4 | * | <2 σ |
| Mandibular Plane Angle(°) | Angle between the Mandibular Plane and the MC-plane | 18.7 | 19.9 | 3.5 | −0.3 | | |
| INTERMAXILLARY | | | | | | | |
| A/P | | | | | | | |
| Intermaxillary Angle(°) | Angle between the Alar Base and ST Pogonion | 0.5 | 3.8 | 3.5 | −0.9 | | > = More Class III |
| Intermaxillary Apical Base Angle(°) | Angle between soft tissue A point and soft tissue B point | 16.7 | 11.5 | 1.7 | 3.0 | *** | > = More Class II |
| Maxillo-Mandibular Differential (mm) | Horizontal distance between Alar Base and ST Pogonion | −2.7 | −3.9 | 2.7 | 0.4 | | |
| Occlusal Plane Angle(°) | Angle between the maxillary occlusal plane and the MA-plane | 9.4 | 15.70 | 3.146624089 | 2.0 | ** | > = Steeper |
| Vertical | | | | | | | |
| Lower Face Height(mm) | Distance from subnasale to soft tissue menton | 74.1 | 65.3 | 6.1 | 1.4 | * | <2 σ |
| Transverse | | | | | | | 90° is = no cant |

TABLE 8A-continued

Analysis Example.

| | Explanation | Value | Norm | SD | Number of Deviations from norm | | comments |
|---|---|---|---|---|---|---|---|
| Maxillary Cant Angle(°) | angle between the maxillary occlusal plane and the MS-angle | 91.5 | 91.0 | 2.8 | 0.2 | | >90° = right side higher |
| | | | | | | | <90° = left side higher |
| DENTAL MEASUREMENTS MAXILLA A/P | | | | | | | |
| Maxillary Incisors (mm) | Perpendicular distance from the maxillary central incisor edge to the MC-plane (right and left average) | 21.1 | 10.1 | 4.0 | 2.8 | ** | <3 σ |
| Maxillary Incisors (°) | Angle between the long axis of the maxillary central incisor an the MC-plane (right and left average) | 102.8 | 95.8 | 3.4 | 2.1 | ** | <3 σ |
| Vertical | | | | | | | |
| Anterior Alveolar Height (mm) | Distance from the incisal edge of the maxillary central incisor to the MA-plane (right and left average) | 25.4 | 24.1 | 3.5 | 0.3 | | <1 σ |
| Posterior Alveolar Height (mm) | Distance from the mesiobuccal cusp of the maxillary first molar to the MA-plane (right and left average) | 21.3 | 19.8 | 4.0 | 0.4 | | <1 σ |
| MANDIBLE A/P | | | | | | | |
| Mandibular Incisors (mm) | Perpendicular distance from the mandibular central incisor edge to the MC-plane (right and left average) | 17.0 | 7.8 | 3.9 | 2.4 | ** | <3 σ |
| Mandibular Incisors (°) | Angle between the long axis of the mandibular central incisor an the MC-plane (right and left average) | 137.1 | 125.7 | 7.3 | 1.6 | * | <2 σ |

What is claimed is:

1. A method for determining a reference standard diagnostic tool comprising:

selecting a set of subjects meeting a first set of aesthetic criteria;

determining a 3 dimensional (3D) representation of a head and mouth of each subject from two or more photographic images of the head and mouth of each subject, the 3D representation including an indication a central point of a left pupil and a right pupil of each subject;

wherein the 3D representation of the head and mouth is determined by indexing a first photographic image to a second photographic image by marking an area in the first photographic image and searching for an area in the second photographic image having a substantially same curvature as the marked area in the first photographic image;

identifying at least one dental feature and at least one facial feature in the 3D representation of the head and mouth of each subject;

identifying at least one landmark on the at least one dental feature and at least one landmark on the at least one facial feature in the 3D representation of the head and mouth of each subject;

defining in the 3D representation of the head and mouth of each subject a mid-axial plane extending horizontally through the central point of both pupils of each subject;

defining in the 3D representation of the head and mouth of each subject a mid-coronal plane extending vertically through the central point of both pupils of each subject;

defining in the 3D representation of the head and mouth of each subject a left sagittal plane extending vertically through the left pupil of each subject;

defining in the 3D representation of the head and mouth of each subject a right sagittal plane extending vertically through the right pupil of each subject;

determining a first dental landmark distance from at least one of the mid-axial plane, the mid-coronal plane, the left sagittal plane, and the right sagittal plane to the at least one landmark on the at least one dental feature; and determining a first facial landmark distance from at least one of the mid-axial plane, the mid-coronal plane, the left sagittal plane, and the right sagittal plane to the at least one landmark on the at least one facial feature.

2. The method according to claim 1 wherein the at least one dental feature includes a tooth and the at least one landmark is a point along a facial axis of a clinical crown of the tooth.

3. The method according to claim 1 wherein the at least one facial feature includes a location on the face of the subject and the at least one landmark is a point midway between the pupils of the subject.

4. The method according to claim 1 wherein the first dental landmark distance is determined as a perpendicular distance from one of the mid-axial plane, the mid-coronal plane, the left sagittal plane, and the right sagittal plane.

5. The method according to claim 1 wherein the first facial landmark distance is determined as a perpendicular distance from one of the mid-axial plane, the mid-coronal plane, the left sagittal plane, and the right sagittal plane.

6. The method according to claim 1 wherein the 3D representation of the head and mouth is determined only using the two or more photographic images.

7. The method according to claim 1 wherein the first photographic image shows a facial image of the subject at rest and the second photographic image shows a smiling facial image of the subject, and the first photographic image is superimposed over the second photograph image by matching the marked area of the first photographic image to the area in the second photographic image having a substantially same curvature as the marked area in the first photographic image, such that when the first photograph image is made transparent any teeth shown in the second transparent image are visible with respect to the facial image of the subject at rest.

8. A method for determining an orthodontic patient treatment plan from reference standard comprising:

determining a 3 dimensional (3D) representation of a head and mouth of the patient from two or more photographic images of the head and mouth of the patient, the 3D representation including an indication a central point of a left pupil and a right pupil of the patient;

wherein the 3D representation of the head and mouth is determined by indexing a first photographic image to a second photographic image by marking an area in the first photographic image and searching for an area in the second photographic image having a substantially same curvature as the marked area in the first photographic image;

identifying at least one dental feature and at least one facial feature in the 3D representation of the head and mouth of the patient;

identifying at least one landmark on the at least one dental feature and at least one landmark on the at least one facial feature in the 3D representation of the head and mouth of the patient;

defining in the 3D representation of the head and mouth of the patient a mid-axial plane extending horizontally through the central point of both pupils of the patient;

defining in the 3D representation of the head and mouth of the patient a mid-coronal plane extending vertically through the central point of both pupils of the patient;

defining in the 3D representation of the head and mouth of the patient a left sagittal plane extending vertically through the left pupil of the patient;

defining in the 3D representation of the head and mouth of the patient a right sagittal plane extending vertically through the right pupil of the patient;

determining a first dental landmark distance from at least one of the mid-axial plane, the mid-coronal plane, the left sagittal plane, and the right sagittal plane to the at least one landmark on the at least one dental feature of the patient;

comparing the first dental landmark distance with a corresponding reference standard distance to determine a deviation from the reference standard distance; and determining a patient treatment plan as a function of the determined deviation from the reference standard distance.

9. The method according to claim 8 wherein the at least one dental feature includes a tooth and the at least one landmark is a point along a facial axis of a clinical crown of the tooth.

10. The method according to claim 8 wherein the first dental landmark distance is determined as a perpendicular distance from one of the mid-axial plane, the mid-coronal plane, the left sagittal plane, and the right sagittal plane.

11. The method according to claim 8 further comprising determining a first dental axis as a line intersecting at least one dental landmark and determining a dental landmark angle as an angle between the first dental axis and one of the mid-axial plane, the mid-coronal plane, the left sagittal plane, and the right sagittal plane.

12. The method according to claim 8 wherein the 3D representation of the head and mouth is determined only using the two or more photographic images.

13. The method according to claim 8 wherein the first photographic image shows a facial image of the subject at rest and the second photographic image shows a smiling facial image of the subject, and the first photographic image is superimposed over the second photograph image by matching the marked area of the first photographic image to the area in the second photographic image having a substantially same curvature as the marked area in the first photographic image, such that when the first photograph image is made transparent any teeth shown in the second transparent image are visible with respect to the facial image of the subject at rest.

14. A method for determining a reference standard diagnostic tool for a subject comprising:

determining a 3 dimensional (3D) representation of a head and mouth of the subject from two or more photographic images of the head and mouth of the subject;

wherein the 3D representation of the head and mouth is determined by indexing a first photographic image to a second photographic image by marking an area in the first photographic image and searching for an area in the second photographic image having a substantially same curvature as the marked area in the first photographic image;

identifying at least one dental feature and at least one facial feature in the 3D representation of the head and mouth of the subject;

identifying at least one landmark on the at least one dental feature and at least one landmark on the at least one facial feature in the 3D representation of the head and mouth of the subject;

defining a first plane in the 3D representation of the head and mouth of the subject;

determining a first dental landmark distance from the first plane to the at least one landmark on the at least one dental feature; and determining a first facial landmark distance from the first plane to the at least one landmark on the at least one facial feature.

15. The method according to claim 14 wherein the first photographic image shows a facial image of the subject at rest and the second photographic image shows a smiling facial image of the subject, and the first photographic image is superimposed over the second photograph image by matching the marked area of the first photographic image to the area in the second photographic image having a substantially same curvature as the marked area in the first photographic image, such that when the first photograph image is made transparent any teeth shown in the second transparent image are visible with respect to the facial image of the subject at rest.

\* \* \* \* \*